United States Patent
Bohlig et al.

(10) Patent No.: US 10,563,144 B2
(45) Date of Patent: *Feb. 18, 2020

(54) SORBENT CONTAINING ENGINEERED FUEL FEED STOCK

(71) Applicant: Accordant Energy, LLC, Rutland, VT (US)

(72) Inventors: James W. Bohlig, Rutland, VT (US); Dingrong Bai, Rutland, VT (US); Paula A. Calabrese, Rutland, VT (US)

(73) Assignee: Accordant Energy, LLC, Rutland, VT (US)

( * ) Notice: Subject to any disclaimer, the term of this patent is extended or adjusted under 35 U.S.C. 154(b) by 60 days.

This patent is subject to a terminal disclaimer.

(21) Appl. No.: 15/669,797

(22) Filed: Aug. 4, 2017

(65) Prior Publication Data
US 2018/0086995 A1 Mar. 29, 2018

Related U.S. Application Data

(60) Continuation of application No. 14/861,768, filed on Sep. 22, 2015, now Pat. No. 9,752,086, which is a
(Continued)

(51) Int. Cl.
*C10L 5/44* (2006.01)
*C10J 3/72* (2006.01)
(Continued)

(52) U.S. Cl.
CPC . *C10J 3/72* (2013.01); *C10L 5/44* (2013.01); *C10L 5/46* (2013.01); *F23G 5/0273* (2013.01);
(Continued)

(58) Field of Classification Search
CPC .................. C10J 3/72; C10J 2300/0996; C10J 2300/0983; C10J 2300/0946; C10L 5/44;
(Continued)

(56) References Cited

U.S. PATENT DOCUMENTS 3,403,643 A 10/1968 Denig
3,642,458 A 2/1972 Hess et al.
(Continued)

FOREIGN PATENT DOCUMENTS

CA 2026828 4/1991
CH 552523 8/1974
(Continued)

OTHER PUBLICATIONS

Supplementary European Search Report for European Application No. 09771071.9, dated May 21, 2012, 7 pages.
(Continued)

*Primary Examiner* — Pamela H Weiss
(74) *Attorney, Agent, or Firm* — Cooley LLP

(57) ABSTRACT

Disclosed are novel engineered fuel feed stocks, feed stocks produced by the described processes, methods of making the fuel feed stocks, methods of producing energy from the fuel feed stocks. Components derived from processed MSW waste streams can be used to make such feed stocks which are substantially free of glass, metals, grit and noncombustibles and contain a sorbent. These feed stocks are useful for a variety of purposes including as gasification and combustion fuels. In addition, one or more sorbents can be added to the feed stocks in order to reduce the amount of a variety of pollutants present in traditional fuel and feed stocks, including, but not limited, sulfur and chlorine. Further, these feed stocks with added sorbent can mitigate corrosion, improve fuel conversion, extend power generating plant lifetime, reduce ash slagging, and reduced operating temperature.

81 Claims, 6 Drawing Sheets

Related U.S. Application Data continuation of application No. 14/086,662, filed on Nov. 21, 2013, now Pat. No. 9,181,508, which is a division of application No. 13/329,028, filed on Dec. 16, 2011, now Pat. No. 8,617,264, which is a division of application No. 12/949,982, filed on Nov. 19, 2010, now Pat. No. 8,382,862.

(60) Provisional application No. 61/289,217, filed on Dec. 22, 2009.

(51) Int. Cl.
   *F23G 5/027* (2006.01)
   *F23K 1/00* (2006.01)
   *C10L 5/46* (2006.01)

(52) U.S. Cl.
   CPC ......... *F23K 1/00* (2013.01); *C10J 2300/0946* (2013.01); *C10J 2300/0983* (2013.01); *C10J 2300/0996* (2013.01); *C10L 2200/029* (2013.01); *F23G 2201/40* (2013.01); *F23G 2201/701* (2013.01); *F23G 2207/60* (2013.01); *F23K 2201/505* (2013.01); *Y02E 20/12* (2013.01); *Y02E 50/10* (2013.01); *Y02E 50/30* (2013.01)

(58) Field of Classification Search
   CPC .... C10L 5/46; C10L 2200/029; F23G 5/0273; F23G 2201/701; F23G 2201/40; F23G 2207/60; F23K 2201/505; F23K 1/00; Y02E 50/30; Y02E 50/10; Y02E 20/12
   See application file for complete search history.

(56) References Cited

U.S. PATENT DOCUMENTS

| | | | |
|---|---|---|---|
| 3,650,711 A | 3/1972 | Unick et al. | |
| 3,759,196 A | 9/1973 | Spaite | |
| 3,790,091 A | 2/1974 | Law et al. | |
| 3,846,096 A | 11/1974 | Malian et al. | |
| 3,905,336 A | 9/1975 | Gamble et al. | |
| 3,910,775 A | 10/1975 | Jackman | |
| 3,950,143 A | 4/1976 | Pyle | |
| 3,961,913 A | 6/1976 | Brenneman et al. | |
| 4,015,951 A | 4/1977 | Gunnerman | |
| 4,026,678 A | 5/1977 | Livingston | |
| 4,049,391 A | 9/1977 | Marsh | |
| 4,052,173 A | 10/1977 | Schultz | |
| 4,072,273 A | 2/1978 | Reiniger | |
| 4,078,902 A | 3/1978 | Olson | |
| 4,152,119 A | 5/1979 | Schulz | |
| 4,153,514 A | 5/1979 | Garrett et al. | |
| 4,193,206 A | 3/1980 | Maffet | |
| 4,201,551 A | 5/1980 | Lvshkow et al. | |
| 4,225,457 A | 9/1980 | Schulz | |
| 4,229,183 A | 10/1980 | Eneroth et al. | |
| 4,230,460 A | 10/1980 | Maust, Jr. | |
| 4,236,897 A * | 12/1980 | Johnston | C10L 5/44 44/491 |
| 4,249,471 A | 2/1981 | Gunnerman | |
| 4,265,636 A | 5/1981 | Frankiewicz | |
| 4,303,412 A | 12/1981 | Baikoff et al. | |
| 4,308,033 A | 12/1981 | Gunnerman | |
| 4,381,718 A | 5/1983 | Carver et al. | |
| 4,395,265 A | 7/1983 | Reilly et al. | |
| 4,398,917 A | 8/1983 | Reilly | |
| 4,405,331 A | 9/1983 | Blaustein et al. | |
| 4,440,635 A | 4/1984 | Reiniger | |
| 4,445,906 A | 5/1984 | Riemann et al. | |
| 4,472,245 A | 9/1984 | Halm et al. | |
| 4,476,816 A | 10/1984 | Cannon et al. | |
| 4,515,601 A | 5/1985 | Charters | |
| 4,529,407 A | 7/1985 | Johnston et al. | |
| 4,588,568 A | 5/1986 | Pollmann et al. | |
| 4,613,339 A | 9/1986 | Gunnerman et al. | |
| 4,624,417 A | 11/1986 | Gangi et al. | |
| 4,624,419 A | 11/1986 | Hevesi et al. | |
| 4,758,244 A | 7/1988 | Harvey et al. | |
| 4,787,917 A | 11/1988 | Leclerc De Bussy | |
| 4,824,441 A * | 4/1989 | Kindig | C10L 9/10 110/347 |
| 4,828,577 A | 5/1989 | Markham, Jr. et al. | |
| 4,867,755 A | 9/1989 | Majid et al. | |
| 4,875,905 A | 10/1989 | Somerville et al. | |
| 4,886,519 A | 12/1989 | Hayes et al. | |
| 5,067,317 A | 11/1991 | Kasper | |
| 5,125,931 A | 6/1992 | Schulz | |
| 5,250,080 A | 10/1993 | Michelena et al. | |
| 5,284,497 A | 2/1994 | Egiebor et al. | |
| 5,342,418 A | 8/1994 | Jesse | |
| 5,368,617 A | 11/1994 | Kindig | |
| 5,369,947 A | 12/1994 | Dummersdorf et al. | |
| 5,387,267 A | 2/1995 | Warf et al. | |
| 5,421,837 A | 6/1995 | Michelena et al. | |
| 5,429,645 A | 7/1995 | Benson et al. | |
| 5,431,702 A | 7/1995 | Schulz | |
| 5,441,990 A | 8/1995 | Robin et al. | |
| 5,470,361 A | 11/1995 | Linke et al. | |
| 5,562,743 A | 10/1996 | Daugherty et al. | |
| 5,591,417 A | 1/1997 | Buchanan et al. | |
| 5,643,342 A | 7/1997 | Andrews | |
| 5,707,417 A | 1/1998 | Yokoyama et al. | |
| 5,711,771 A | 1/1998 | Brown | |
| 5,755,836 A | 5/1998 | Beyer | |
| 5,797,972 A | 8/1998 | Schulz | |
| 5,888,256 A | 3/1999 | Morrison | |
| 5,916,826 A | 6/1999 | White | |
| 5,980,595 A | 11/1999 | Andrews | |
| 6,000,639 A | 12/1999 | Ganguli | |
| 6,001,143 A | 12/1999 | Rees et al. | |
| 6,048,374 A | 4/2000 | Green | |
| 6,149,694 A | 11/2000 | Redden, Jr. et al. | |
| 6,152,306 A | 11/2000 | Miller | |
| 6,152,974 A | 11/2000 | Delpiano et al. | |
| 6,165,238 A | 12/2000 | Parkinson et al. | |
| 6,214,064 B1 | 4/2001 | Boss et al. | |
| 6,352,956 B1 | 3/2002 | Kienow et al. | |
| 6,401,635 B1 | 6/2002 | Nieminen et al. | |
| 6,409,798 B1 | 6/2002 | Nieminen et al. | |
| 6,423,878 B2 | 7/2002 | Reverso | |
| 6,506,223 B2 | 1/2003 | White | |
| 6,522,994 B1 | 2/2003 | Lang | |
| 6,582,486 B1 | 6/2003 | Delpiano et al. | |
| 6,635,093 B1 | 10/2003 | Schoen et al. | |
| 6,692,544 B1 | 2/2004 | Grillenzoni | |
| 6,780,210 B2 | 8/2004 | Boss et al. | |
| 6,790,383 B2 | 9/2004 | Kim et al. | |
| 7,028,478 B2 | 4/2006 | Prentice, III | |
| 7,247,285 B2 | 7/2007 | Zauderer | |
| 7,252,691 B2 | 8/2007 | Philipson | |
| 7,276,217 B2 | 10/2007 | Radway et al. | |
| 7,314,002 B2 | 1/2008 | Dupuis | |
| 7,334,345 B2 | 2/2008 | Lasonde | |
| 7,431,156 B2 | 10/2008 | Carlsson | |
| 7,468,170 B2 | 12/2008 | Comrie | |
| 7,507,083 B2 | 3/2009 | Comrie | |
| 7,674,442 B2 | 3/2010 | Comrie | |
| 7,758,827 B2 | 7/2010 | Comrie | |
| 7,776,301 B2 | 8/2010 | Comrie | |
| 7,955,577 B2 | 6/2011 | Comrie | |
| 7,988,939 B2 | 8/2011 | Comrie | |
| 8,157,874 B2 * | 4/2012 | Bohlig | C10J 3/463 44/589 |
| 8,157,875 B2 * | 4/2012 | Bohlig | C10J 3/463 44/589 |
| 8,192,512 B2 | 6/2012 | Bohlig et al. | |
| 8,192,513 B2 * | 6/2012 | Bohlig | C10J 3/463 44/589 |
| 8,349,034 B2 | 1/2013 | Calabrese et al. | |
| 8,382,862 B2 | 2/2013 | Bohlig et al. | |
| 8,382,863 B2 | 2/2013 | Bohlig et al. | |
| 8,444,721 B2 | 5/2013 | Bai | |

(56) References Cited

U.S. PATENT DOCUMENTS

| | | | |
|---|---|---|---|
| 8,523,962 B2 | 9/2013 | Bohlig et al. | |
| 8,579,997 B2* | 11/2013 | Bai | C10L 5/06 44/589 |
| 8,585,787 B2 | 11/2013 | Bai et al. | |
| 8,617,264 B2 | 12/2013 | Bohlig et al. | |
| 8,746,599 B2* | 6/2014 | Bai | C10L 5/06 241/29 |
| 8,828,105 B2 | 9/2014 | Calabrese et al. | |
| 8,852,302 B2* | 10/2014 | Bai | C10L 5/36 44/605 |
| 8,906,119 B2 | 12/2014 | Bohlig et al. | |
| 8,999,014 B2 | 4/2015 | Bai | |
| 9,062,268 B2* | 6/2015 | Bai | C10L 5/36 |
| 9,126,204 B1 | 9/2015 | Toberman et al. | |
| 9,181,508 B2* | 11/2015 | Bohlig | C10L 5/46 |
| 9,487,722 B2 | 11/2016 | Bai et al. | |
| 9,523,051 B2 | 12/2016 | Bai et al. | |
| 9,688,931 B2 | 6/2017 | Bai et al. | |
| 9,752,086 B2 | 9/2017 | Bohlig et al. | |
| 9,765,269 B2* | 9/2017 | Bohlig | B29B 17/02 |
| 10,174,268 B2* | 1/2019 | Bai | C10L 9/10 |
| 10,329,501 B2 | 6/2019 | Bai et al. | |
| 2002/0025285 A1 | 2/2002 | Comparato et al. | |
| 2002/0184816 A1 | 12/2002 | Philipson | |
| 2003/0106467 A1 | 6/2003 | Jones, Jr. | |
| 2004/0050678 A1 | 3/2004 | Takahashi et al. | |
| 2004/0141891 A1 | 7/2004 | Abe et al. | |
| 2004/0237405 A1 | 12/2004 | Takeuchi et al. | |
| 2004/0244289 A1 | 12/2004 | Morozumi et al. | |
| 2005/0050799 A1 | 3/2005 | Buchanan et al. | |
| 2005/0074380 A1 | 4/2005 | Boren et al. | |
| 2006/0053791 A1 | 3/2006 | Prentice, III | |
| 2006/0096163 A1 | 5/2006 | Dickinson et al. | |
| 2006/0112616 A1 | 6/2006 | Noll et al. | |
| 2006/0120933 A1 | 6/2006 | Boardman et al. | |
| 2006/0123697 A1 | 6/2006 | Jansen | |
| 2006/0194990 A1 | 8/2006 | Miyoshi et al. | |
| 2006/0228294 A1 | 10/2006 | Davis et al. | |
| 2006/0254957 A1 | 11/2006 | Bohlig et al. | |
| 2006/0265954 A1 | 11/2006 | Dogru et al. | |
| 2007/0004809 A1 | 1/2007 | Lattner et al. | |
| 2007/0006526 A1 | 1/2007 | Cullen | |
| 2007/0140943 A1 | 6/2007 | Comrie | |
| 2007/0173673 A1 | 7/2007 | Fujimoto et al. | |
| 2007/0204512 A1 | 9/2007 | Self et al. | |
| 2007/0261295 A1 | 11/2007 | Tolmie | |
| 2008/0014112 A1 | 1/2008 | Lee et al. | |
| 2008/0060519 A1 | 3/2008 | Maly et al. | |
| 2008/0110090 A1 | 5/2008 | Zawadzki et al. | |
| 2008/0121142 A1 | 5/2008 | Comrie et al. | |
| 2008/0193351 A9 | 8/2008 | Boardman et al. | |
| 2008/0233029 A1 | 9/2008 | Fan et al. | |
| 2008/0237093 A1 | 10/2008 | Bohlig et al. | |
| 2008/0286703 A1 | 11/2008 | Comrie et al. | |
| 2008/0290006 A1 | 11/2008 | Duffy et al. | |
| 2009/0020405 A1 | 1/2009 | Fan et al. | |
| 2009/0056205 A1 | 3/2009 | Gauthier et al. | |
| 2009/0056206 A1 | 3/2009 | Gauthier et al. | |
| 2009/0099038 A1 | 4/2009 | Deisseroth et al. | |
| 2010/0018113 A1 | 1/2010 | Bohlig et al. | |
| 2010/0031560 A1 | 2/2010 | Calabrese et al. | |
| 2010/0144905 A1 | 6/2010 | Reaveley et al. | |
| 2010/0218419 A1 | 9/2010 | Bai | |
| 2010/0263577 A1 | 10/2010 | Nijhawan | |
| 2010/0323308 A1 | 12/2010 | Comrie | |
| 2011/0099890 A1 | 5/2011 | Bohlig et al. | |
| 2011/0209393 A1 | 9/2011 | Bohlig et al. | |
| 2011/0209394 A1 | 9/2011 | Bohlig et al. | |
| 2011/0209395 A1 | 9/2011 | Bohlig et al. | |
| 2011/0209396 A1 | 9/2011 | Bohlig et al. | |
| 2011/0209397 A1 | 9/2011 | Bohlig et al. | |
| 2011/0209398 A1 | 9/2011 | Bohlig et al. | |
| 2011/0209399 A1 | 9/2011 | Bohlig et al. | |
| 2012/0210633 A1 | 8/2012 | Bohlig et al. | |
| 2012/0304536 A1 | 12/2012 | Bai | |
| 2013/0097921 A1 | 4/2013 | Calabrese et al. | |
| 2013/0298454 A1 | 11/2013 | Bai | |
| 2014/0096441 A1 | 4/2014 | Bai et al. | |
| 2014/0157659 A1 | 6/2014 | Bohlig et al. | |
| 2015/0096222 A1 | 4/2015 | Calabrese et al. | |
| 2015/0197698 A1 | 7/2015 | Bohlig et al. | |
| 2016/0002546 A1 | 1/2016 | Bai | |
| 2016/0108328 A1 | 4/2016 | Bohlig et al. | |
| 2017/0073599 A1 | 3/2017 | Bai et al. | |
| 2017/0114292 A1 | 4/2017 | Bai et al. | |
| 2017/0137729 A1 | 5/2017 | Bai et al. | |

FOREIGN PATENT DOCUMENTS

| | | |
|---|---|---|
| CN | 1396245 A | 2/2003 |
| CN | 1623698 A | 6/2005 |
| CN | 1224683 C | 10/2005 |
| CN | 1914463 | 2/2007 |
| CN | 101134922 A | 3/2008 |
| CN | 101215490 | 7/2008 |
| CN | 101360548 | 2/2009 |
| CN | 101495603 | 7/2009 |
| DE | 3409862 | 9/1985 |
| DE | 69314835 | 3/1998 |
| EP | 0325309 | 7/1989 |
| EP | 0423859 | 4/1991 |
| EP | 0512721 | 11/1992 |
| EP | 0566419 | 10/1993 |
| EP | 0568345 | 2/1997 |
| EP | 1072671 | 1/2001 |
| EP | 1167494 | 1/2002 |
| EP | 1083212 B1 | 11/2004 |
| EP | 2298082 | 3/2011 |
| EP | 2134820 B1 | 9/2011 |
| EP | 2307531 B1 | 2/2012 |
| FR | 2818657 | 6/2002 |
| JP | S58-061181 | 4/1983 |
| JP | H05-132683 | 5/1993 |
| JP | H07-179871 | 7/1995 |
| JP | H10-235313 | 9/1998 |
| JP | H10-244237 | 9/1998 |
| JP | 2003-253037 | 9/2003 |
| JP | 2005-290129 | 10/2005 |
| JP | 2008-106270 | 5/2008 |
| JP | 2011-526323 | 10/2011 |
| KR | 20000012536 | 3/2000 |
| WO | WO 2000/000574 | 1/2000 |
| WO | WO 2000/000575 | 1/2000 |
| WO | WO 2002/051969 | 7/2002 |
| WO | WO 2005/097684 | 10/2005 |
| WO | WO 2006/053020 | 5/2006 |
| WO | WO 2006/099611 | 9/2006 |
| WO | WO 2007/084509 | 7/2007 |
| WO | WO 2007/123510 | 11/2007 |
| WO | WO 2007/147244 | 12/2007 |
| WO | WO 2008/100243 | 8/2008 |
| WO | WO 2008/107042 | 9/2008 |
| WO | WO 2009/158539 | 12/2009 |
| WO | WO 2009/158540 | 12/2009 |
| WO | WO 2010/013202 | 2/2010 |
| WO | WO 2011/078928 | 6/2011 |
| WO | WO 2011/084730 | 7/2011 |
| WO | WO 2013/113026 | 8/2013 |

OTHER PUBLICATIONS

International Search Report and Written Opinion for International Application No. PCT/US2009/048718, dated Aug. 13, 2009, 9 pages.
European Search Report for European Application No. 17166365.1, dated Jun. 13, 2017, 8 pages.
Supplementary European Search Report for European Application No. 09771072.7, dated May 21, 2012, 7 pages.
International Search Report and Written Opinion for International Application No. PCT/US2009/048719, dated Sep. 16, 2009, 9 pages.
Supplementary European Search Report for European Application No. 16206883.7, dated May 10, 2017, 6 pages.

(56) References Cited

OTHER PUBLICATIONS

International Search Report and Written Opinion for International Application No. PCT/US2010/061228, dated Feb. 22, 2011, 14 pages.
Search Report for Chinese Patent Application No. 201080064580.0, dated Mar. 21, 2014.
Supplementary European Search Report for European Application No. 10839960.1, dated Oct. 4, 2013, 8 pages.
International Search Report and Written Opinion for International Application No. PCT/US2010/057351, dated Feb. 2, 2011.
European Search Report and Search Opinion for European Application No. 17163242.5, dated Aug. 1, 2017, 8 pages.
International Search Report and Written Opinion for International Application No. PCT/US2012/022786, dated May 1, 2012, 8 pages.
Supplementary European Search Report for European Application No. 13740783.9, dated Jul. 9, 2015, 8 pages.
International Search Report and Written Opinion for International Application No. PCT/US2013/023498, dated Aug. 7, 2013, 12 pages.
Complaint for Patent Infringement filed by Accordant Energy, LLC, *Accordant Energy, LLC v. Vexor Technology, Inc. et al.*, In The United States District Court for the Northern District of Ohio Eastern Division, Civil Action No. 1:17-cv-411, filed Feb. 28, 2017, 21 pages.
Amended Answer and Counterclaims filed by Vexor Technology, Inc. and Vexor Technology, LLC, *Accordant Energy, LLC v. Vexor Technology, Inc. et al.*, In The United States District Court for the Northern District of Ohio Eastern Division, Civil Action No. 1:17-cv-411, filed May 18, 2017, 49 pages.
Arena, U. et al., "Gasification of a Plastic Waste in a Pilot Fluidized Bed Reactor," 7 pages, 10th Conference on Process Integration, Modelling and Optimisation for Energy Saving and Pollution Reduction, Ischia Island, Gulf of Naples, Jun. 24-27, 2007.
Aznar et al., "Plastic waste elimination by co-gasification with coal and biomass in fluidized bed with air in pilot plant," Fuel Processing Technology 87(5):409-420 (2006).
Biobib, "paper," "waste, domestic organic waste from the municipal collection," "douglas fir," and "wood, sawdust," 12 pages, from BIOBIB a Data Base for Biofuels (www.vt.tuwien.ac.at/biobib/biobib.html information available online 2007 and earlier).
Blasi, "Influence of physical properties on biomass devolitilization characteristics," Fuel, 76(10):957-964 (1997).
Boavida, D. et al., "Co-combustion of coal and non-recyclable paper and plastic waste in a fluidised bed reactor," Fuel, 82 (2003) 1931-1938.
Bourgois et al., "Characterization and analysis of torrefied wood," Wood Sci. Technol., 22:143-155 (1988).
Buckley, T. J. et al., "Evaluation of data on higher-heating values and elemental analysis for refuse derived fuels," National Waste Processing Conf., PA, USA pp. 16-24 (1988), discussions and author's reply.
Buckley, T. J. et al., "Evaluation of data on higher-heating values and elemental analysis for refuse derived fuels," National Waste Processing Conf., PA, USA pp. 77-84 (1988).
Canova, J. H., "Testing and Evaluating the Combustion Characteristics of Waste Fuels," Thesis in Mechanical Engineering (May 1992), 120 pages.
Cozzani, V. et al., "Devolatilization and pyrolysis of refuse derived fuels: characterization and kinetic modelling by a thermogravimetric and calorimetric approach," Fuel, 74(6):903-912 (1995).
Fisher, M. M. et al., "Processed engineered fuels derived from paper and plastic—Techno-economic factors and regulatory issues in a competitive market," Proceedings of Fifth Annual North American Waste-to-Energy Conference, Research Triangle Park, North Carolina, Apr. 22-25, 1997, pp. 475-488.
Frost, M., "Tires as a fuel supplement: feasibility study," 1992, pp. 1-120.
Hasselriis, F., "Refuse-Derived Fuel Processing," Butterworth Publishers, 1984, pp. 1-340.
Hasselriis, F., "Refuse-Derived Fuel Processing," Butterworth Publishers, 1984, pp. 275-298.
Kreith, F. et al. (eds.), "The CRC Handbook of Mechanical Engineering," Second Edition, Jan. 2004, CRC Press, Chapter 7, p. 7-32.
Monti, A. (ed.), Green Energy and Technology, Switchgrass: A Valuable Biomass Crop for Energy, pp. 170-171 (2012).
Phyllis Database, "Elemental content," [online], URL: <http://www.ecn.nl/phyllis/>, See ECN Phyllis Classification Bagasse #1481, (1998), 6 pages.
Pinto, F. et al., "Pyrolysis of plastic wastes. 1. Effect of plastic waste composition on product yield," Journal of Analytical and Applied Pyrolysis, 51(1-2):39-55 (Jul. 1999).
Prins, M. J. et al., "From coal to biomass gasification: Comparison of thermodynamic efficiency," Energy 32:1248-1259 (2007).
Ragland, K. W. et al., "Properties of wood for combustion analysis," Bioresource Technology, 37(2):161-168 (1991).
Sami, M., "Co-Firing of Coal and Biomass Fuel Blends," Progress in Energy and Combustion Science, 27(2):171-214 (2001).
Sorum, L. et al., "Pyrolysis characteristics and kinetics of municipal solid wastes," Fuel, 80:1217-1227 (Jul. 2001).
Sun, M., "Study on the preparation of RDF by mixing waste of high calorific value and biomass and the combustion characteristic thereof," Chinese Master's Dissertations Full-Text Database, Engineering Technology, Edition I, vol. 10, p. B027-214 (Oct. 15, 2009).
Tomczyck, L., "Engineered Fuel: Renewable Fuel of the Future?," Solid Waste Technologies, Jan./Feb. 1997, 10 pages.
UNEP: "Waste characterization and quantification with projections for future," Developing Integrated Solid Waste Management Plan, Jan. 1, 2009, pp. 1-27, Osaka Japan, Retrieved from the Internet: <URL: http://www.unep.or.jp/ietc/Publications/spc/ISWMPlan_Vol1.pdf> [retrieved on Sep. 20, 2013), 77 pages.
Wu, C-H et al., "On the thermal treatment of plastic mixtures of MSW: Pyrolysis kinetics," Waste Management, vol. 13, Jan. 1993, pp. 221-235.
Xie, Q. et al., Municipal Solid Waste Energy Utilization Technology, Chemical Industry Press, First Edition (2004), pp. 78-80.
Even, J. C. et al., "Evaluation of the Ames Solid Waste Recovery System, Part I, Summary of Environmental Emissions: Equipment, Facilities, and Economic Evaluations," EPA-600/2-77-205 (Nov. 1977).
Fiscus, D. E. et al., "Evaluation of the Performance of the Disc Screens Installed at the City of Ames, Iowa Resource Recovery Facility," Proc. ASME National Waste Processing Conf., Washington, DC, 1980.
Fiscus, D. E. et al., "Study of Existing RDF-Cofiring Experience, vol. 3: Phase II Final Report," ANL/CNSV-TM-134, vol. 3, Oct. 31, 1983.
Refuse Derived Fuel, Current Practice and Perspectives (B4-3040/2000/306517/MAR/E3) Final Report No. CO 5087-4, Jul. 2003.
Garg, A. et al., "Wastes as Co-Fuels: the Policy Framework for Solid Recovered Fuel (SRF) in Europe, with UK Implications," Environ. Sci. Technol., 41(14):4868-4874 (2007).
Raghunathan, K. et al., "Prevention of PCDD/PCDF Formation by Coal Co-Firing," U.S. Environmental Protection Agency, Air Pollution Prevention and Control Division (1998), pp. 779-793.
Fritsky, K. J. et al., "Methodology for Modeling the Devolatilization of Refuse-Derived Fuel from Thermogravimetric Analysis of Municipal Solid Waste Components," J. Air & Waste Manage. Assoc. 44:9, 1116-1123 (1994).
U.S. Environmental Protection Agency, Cement Sector, Trends in Beneficial Use of Alternative Fuels and Raw Materials, Oct. 2008, 117 pages.
Wan Ab Karim Ghani, Azlina. Co-combustion of biomass fuels with coal in a fluidised bed combustor. Diss. University of Sheffield, 2006.
Psomopoulos, C.S. A. Bourka and N.J. Themelis, "Waste to energy: A review of the status and benefits in U.S.A.", CEMEPE07, Skiathos, Greece, Jun. 2007.
Psomopoulos, C. S., A. Batakis, and J. Daskalakis. "Residue derived fuels production in Greece: an alternative fuel for the power generation sector based in EU and international experience," Sixth

(56) References Cited

OTHER PUBLICATIONS

Mediterranean Conference and Exhibition on Power Generation, Transmission and Distribution, IET Hellas (MedPower 2008), Thessaloniki. 2008.

Kilgroe, J. Municipal-waste combustion study: combustion control of organic emissions. Final report. No. PB-87-206090/XAB. Energy and Environmental Research Corp., Irvine, CA (USA), 1987.

Opposition Against European Patent No. 2300575 filed by DREISS Patentanwalte PartGmbB, filed Jan. 23, 2018, 30 pages.

Extended European Search Report for European Application No. 18182688.4, dated Jan. 31, 2019, 10 pages.

ASTM International, Designation: D3176-09, Standard Practice for Ultimate Analysis of Coal and Coke (2012), 4 pages.

ASTM International, Designation: D5373-08, Standard Test Methods for Instrumental Determination of Carbon, Hydrogen, and Nitrogen in Laboratory Samples of Coal (2012), 9 pages.

Bailie, R. C. et al., "Solid Waste," Chapter 10, 1999, CRC Press LLC, 108 pages.

United States Environmental Protection Agency, "Characterization of Municipal Solid Waste in the United States: 1998 Update," (1999), 174 pages.

\* cited by examiner

SORBENT CONTAINING ENGINEERED FUEL FEED STOCK

This application is a continuation of and claims priority to U.S. application Ser. No. 14/861,768, now U.S. Pat. No. 9,752,086, filed Sep. 22, 2015, entitled "SORBENT CONTAINING ENGINEERED FUEL FEED STOCK," which is a continuation of and claims priority to U.S. application Ser. No. 14/086,662, now U.S. Pat. No. 9,181,508, filed Nov. 21, 2013, entitled "SORBENT CONTAINING ENGINEERED FUEL FEED STOCK," which is a divisional of and claims priority to U.S. application Ser. No. 13/329,028, now U.S. Pat. No. 8,617,264, filed Dec. 16, 2011, entitled "SORBENT CONTAINING ENGINEERED FUEL FEED STOCK," which is a divisional of and claims priority to U.S. application Ser. No. 12/949,982, now U.S. Pat. No. 8,382,862, filed Nov. 19, 2010, entitled "SORBENT CONTAINING ENGINEERED FUEL FEED STOCK," which claims priority to and the benefit of U.S. Provisional Patent Application Ser. No. 61/289,217, filed on Dec. 22, 2009, entitled "SORBENT CONTAINING ENGINEERED FUEL FEED STOCK," all of which are hereby incorporated by reference in their entirety for all purposes.

FIELD OF THE INVENTION

The present invention relates to alternative fuels. In particular, the invention relates to engineering fuel feed stock to control emission profiles, corrosion prevention, and operation performance improvements during combustion and gasification applications. The feed stock described herein comprises at least one component of processed municipal solid waste, a sorbent, and optionally other components.

BACKGROUND OF THE INVENTION

Sources of fossil fuels useful for heating, transportation, and the production of chemicals as well as petrochemicals are becoming increasingly more scarce and costly. Industries such as those producing energy and petrochemicals are actively searching for cost-effective engineered fuel feed stock alternatives for use in generating those products and many others. Additionally, due to the ever increasing costs of fossil fuels, transportation costs for moving engineered fuel feed stocks for production of energy and petrochemicals is rapidly escalating.

These energy and petrochemical producing industries, and others, have relied on the use of fossil fuels, such as coal and oil and natural gas, for use in combustion and gasification processes for the production of energy, for heating and electricity, and the generation of synthesis gas used for the downstream production of chemicals and liquid fuels, as well as an energy source for turbines.

Combustion and gasification are thermochemical processes that are used to release the energy stored within the fuel source. Combustion takes place in a reactor in the presence of excess air, or excess oxygen. Combustion is generally used for generating steam which is used to power turbines for producing electricity. However, the brute force nature of the combustion of fuel causes significant amounts of pollutants to be generated in the gas produced. For example, combustion in an oxidizing atmosphere of, for example, fossil fuels such as coal, oil and natural gas, releases nitrogen oxides, a precursor to ground level ozone which can stimulate asthma attacks. Combustion is also the largest source of sulfur dioxide, which in turn produces sulfates that are very fine particulates. Fine particle pollution from U.S. power plants cuts short the lives of over 30,000 people each year. Hundreds of thousands of Americans suffer from asthma attacks, cardiac problems and upper and lower respiratory problems associated with fine particles from power plants.

Gasification also takes place in a reactor, although in the absence of air, or in the presence of substochiometric amounts of oxygen. The thermochemical reactions that take place in the absence of oxygen or under substochiometric amounts of oxygen do not result in the formation of nitrogen oxides or sulfur oxides. Therefore, gasification can eliminate much of the pollutants formed during the firing of fuel.

Gasification generates a gaseous, fuel rich product known as synthesis gas (syngas). During gasification, two processes take place that convert the fuel source into a useable fuel gas. In the first stage, pyrolysis releases the volatile components of the fuel at temperatures below 600° C. (1112° F.), a process known as devolatization. The pyrolysis also produces char that consists mainly of carbon or charcoal and ash. In the second gasification stage, the carbon remaining after pyrolysis is either reacted with steam, hydrogen, or pure oxygen. Gasification with pure oxygen or steam results in a high quality mixture of carbon monoxide and hydrogen due to no dilution of nitrogen from air.

One potential source for a large amount of feed stock for gasification is waste. Waste, such as municipal solid waste (MSW), is typically disposed of or used in combustion processes to generate heat and/or steam for use directly for heating or cooling, or in turbines for power generation. Fuels derived waste streams are often called refuse-derived fuels or RDF. The drawbacks accompanying combustion have been described above, including the production of pollutants such as nitrogen oxides, sulfur oxide, particulates and products of chlorine that damage the environment.

Hydrogen chloride (HCl) (along with other acid gaseous pollutants) is currently emitted in significant quantities by utility and industrial coal-fired furnaces, as well as by municipal, medical and hazardous waste incinerators. Coal contains only traces of chlorine, but electric utility furnaces burn large amounts of coal. In the case of waste incinerators, chlorine is contained in large amounts in some plastic wastes, such as poly(vinyl chloride) (PVC) ($C_2H_3Cl$) and poly(vinylidene chloride) (PVDC) ($C_2H_2Cl_2$), as well as in some food and yard wastes. During pyrolysis of PVC and PVDC, chlorine evolves mostly as HCl, in the preliminary stages of combustion under 350° C. (Panagiotou, T., Levendis, Y. A., 1996. Combust. Sci. Technol. 112, 117, 1996). Capture of HCl is important because it is harmful, corrosive and an acid rain contributor and emissions of HCl are currently regulated (Fellows, K. T., Pilat, M. J., *J. Air Waste Manag. Assoc.* 40, 887, 1990). Moreover, HCl, either directly, or indirectly through the production of chlorine ($Cl_2$ by the Deacon reaction), may contribute to subsequent formation of chlorinated unburned hydrocarbons, polychlorinated dibenzo-dioxins, and polychlorinated dibenzo-furans in the furnace effluent, (Addink, R., Bakker, W. C. M., Olie, K., *Environ. Sci. Technol.* 2055, 1995). Thus, capture of HCl is imperative. To avoid the production of the highly toxic dioxins and furans, which form as the effluent cools, the capture of chlorinated species must take place at high temperatures, preferably above 500° C. Formation of polychlorinated dibenzo-dioxins and furans (PCDD/PCDF) occurs in the fly ash, as the effluent stream cools down to moderate temperatures (≈300° C.) (Stieglitz, L., Zwick, G., Beck, J., Roth, W., Vogg, H., *Chemosphere* 18, 1219, 1989).

Sulfur dioxide emissions related to industrial operations primarily occur from combustion sources and thermal processes, such as power plants (coal or oil fired), incinerators, steam generation equipment, process heaters, chemical reactors, and other similar equipment. All these emission must follow Environmental Protection Agency ("EPA") regulations set by the 1990 Clean Air Act Amendment. Recently, as the construction of new power generation facilities is emphasized and most of the facilities have plans to use coal, a renewed and more interest in economical methods of $SO_2$ emissions will be needed. (Wu, C., Khang, S.-J., Keener, T. C., and Lee, S.-K., Adv. Environ. Research, 8, 655-666, 2004). It is reported that more than 250 techniques for flue gas desulfurization (FGD) have been proposed or developed on a worldwide basis (Oxley, J. H., Rosenberg, H. S., Barrett, R. E., *Energy Eng.* 88, 6, 1991). However, relatively few of those processes are currently in use because of low efficiency (Makansi, J., Power, 137, 23-56, 1993).

Normally fuels and waste containing significant amounts of sulfur or chlorine are not preferred for combustion and gasification reactions. Significant amounts are defined as an amount that when added to a final fuel feed stock causes the final feed stock to have more than 2% sulfur or more than 1% chlorine. For example, materials such as high sulfur containing coal, used tires, carpet, rubber, and certain plastics such as PVC, when combusted, release unacceptable amounts of harmful sulfur- and chlorine-based gases. For this reason, this material is usually avoided as a source of fuel.

Over years the literature has extensively reported that chloride induced corrosion of high temperature surfaces in boilers is one of the most costly problems in the industry. This problem can result in downtime and periodic total shutdowns of the plants, which accounts for a significant fraction of the operating and maintenance cost. It leads to replacement of super-heater pendants as often as annually in some units or the costly use of higher alloyed materials to either shield the metal surfaces or serve as replacement tube material.

The corrosion problem is more severe when biomass and waste derived fuels are used due to the fact that the ash of the biomass and waste fuels has a very different composition and different melting characteristics than the ash of coal. This difference in the ash results in corrosion and chloride salts deposits on the super heater tubes and other parts being comprised in the heat transferring devices of the plants. The corrosion from chlorine begins at steam temperatures in the super-heater of approx. 480° C. (900° F.), and increases along with the temperature up to approx. 500-600° C. (930-1100° F.). This in fact limits the super heated steam temperature in biomass to energy and waste to energy, and consequently limits the power generating efficiency plants as compared to coal fired plants.

Biomass and fossil fuels often contain multiple chemical elements in different proportions that could give rise to various environmental or technological problems during or after they are used as an energy source. Such chemical elements include other halogen gases (i.e., Cl, F, and Br), nitrogen (N), trace metals and mercury (Hg). A higher content of sulfur, chorine, or fluorine, causes serious corrosion of system equipment and creates the hazardous air pollutants as discussed above. Trace elements may also form a threat to the environment or to human health (e.g., Hg, Cd, Pb, As, Cr, Tl), they may cause additional corrosion problems (e.g., Na, K, V, Zn, Pb), and lead to fouling of the turbine blades (mainly Ca) or pollute or poison any catalysts used (mainly As) or sorbents downstream. To avoid or minimize these problems these elements, and/or products formed from these elements that may be liberated or produced during or after the conversion processes (e.g., gasification, combustion), one or more suitable technologies need to be in place to reduce their presence in fuels thereof or process products (gas, liquid or solid).

The systems that have previously been developed or implemented for gas cleaning in gasification and/or combustion processes focus on the control of these pollutants in the actual fuel itself (i.e., by limiting the use of highly polluted fuels) or by controlling the release into the atmosphere by post treatments on the flue gas stream, for example the addition of sorbents. Sorbents such as hydrated lime, calcium carbonate, sodium sesquicarbonate, sodium bicarbonate, and magnesium oxide have been injected into combustion exhaust stack gases in an effort to clean the exit gases of chlorine and sulfur containing pollutants (U.S. Pat. Nos. 6,303,083, 6,595,494, 4,657,738, and 5,817,283). However, these dry sorbents optimally work at temperatures of 800° C. to about 2000° C. and thus have only been used in the exhaust stacks or combustion units. If sorbents such as limestone are used at temperatures below 800° C. then less than 20% conversion of the pollutants occur resulting sometimes in toxic products. Therefore, these sorbents are often made in slurry form and are used in semi-dry/wet and wet scrubbers, which requires more complicated systems and operate with waste water generation, leading to higher capital and operation costs. Gasification of biomass or MSW derived fuels is usually performed at temperatures at or below 850° C. Sorbents have not been heretofore mixed in solid fuel feed stocks comprising at least one component of processed municipal solid waste.

Thus, there is a need for methods that allow the use of various fuel feed stocks in combustion or gasification applications, which otherwise cannot be used due to significant amounts of pollutants produced upon combustion and gasification.

It is an object of the present invention to provide engineered fuel feed stocks comprising sorbents which allow the use of waste materials that contain significant levels of sulfur or chlorine for combustion or gasification applications.

It is a further object of the present invention to provide engineered fuel feed stocks comprising one or more sorbents that can be used to control a specific pollutant, or preferably a number of pollutants at the same time. In order to achieve multiple pollutant control, a multi-functional sorbent is ideally required; alternatively, multiple sorbents could be utilized with each sorbent being selected to treat for a particular element. Selection of sorbents is dependent on a various considerations, including, but not limited to, the following: (i) fuel characteristics, essentially what type and amount of the pollutants need to be controlled by sorbent(s); (ii) operating conditions, such as reducing or oxidizing environment, temperature, pressure, and conversion technologies (e.g., fixed bed, dense fluidized bed, circulating fluidized bed, etc.); (iii) reactivity of the sorbent and characteristics of the by-products, e.g., stability, melting point, boiling point, and toxicity; and (iv) economic effectiveness.

A further object of the invention is to provide sorbent-integrated engineered fuel feed stocks with several distinct advantages, including, but not limited to, the following, improved reaction kinetics, improved sorbent reactivity, improved pollutant removal efficiency, improved fuel conversion, improved corrosion control, reduced ash slagging, reduced operating temperature, extend power generating facility lifetime, avoid expensive retrofit costs, reduced operating and maintenance costs.

With sorbents embedded within the feed stock, an intimate contact between sorbent and pollutant can be achieved where they are generated. Compared to furnace injection in which the pollutant has migrated from within fuel particles to the bulk fuel or flue gas stream, the concentration of the pollutant is higher within the particles when the sorbent is part of the fuel. This configuration improves the reaction kinetics, thus enhancing the reaction.

Further, due to the temperature gradient across the fuel particles, sintering of sorbent inside the fuel particles is reduced, and thus sorbent reactivity is higher.

Combining the sorbent with feed stock to form an integrated fuel particle also allows the use of fine sorbent particles (e.g., <1 µm) while still achieving long residence time in the reaction chamber, which could be on the order of minutes, compared to only 1-2 seconds in case of furnace injection. Together, fine sorbent particles and long residence time would significantly increase the pollutant removal efficiency.

In cases where incompletely reacted sorbents may separate from the fuel particle and get into the flue gas stream, continuous reaction with $H_2S$ (or $SO_2$) in gas stream will continue. As a result, the sorbent utilization will be greatly improved.

Because the sorbent is part of the fuel feed stock, there is no need to have the sorbent handling systems that are normally required for dry sorbent injection systems (storage, delivery, atomizing, etc.).

Also, the products of the sorbent/pollutant reaction mostly remain in the bottom ash, therefore the particulate, or dust, load on downstream collectors (i.e., electrostatic precipitator, baghouse, particulate matter scrubber) would be reduced, resulting savings in capital, operation and maintenance costs otherwise required for these devices.

For gasification, sorbent material can also catalytically improve the fuel conversion, and thus the gasification rate and performance can be enhanced (J. Weldon, G. B. Haldipur, D. A. Lewandowski, K. J. Smith, "Advanced coal gasification and desulfurization with calcium-based sorbent", KRW Energy Systems Inc., Madison, Pa. 15663.)

SUMMARY OF THE INVENTION

The present disclosure describes an engineered fuel feed stock comprising at least one component derived from a processed MSW waste stream and a sorbent, the feed stock possessing a range of chemical molecular characteristics which make it useful for a variety of combustion and gasification purposes. The feed stock can be in the form of loose material, densified cubes, briquettes, pellets, honeycomb, sheets, or other suitable shapes and forms. A process of producing engineered fuel feed stock comprising at least one component derived from a processed MSW waste stream and a sorbent, is described which comprises the process in which a plurality of waste streams, including solid and liquid wastes, are processed and, where necessary, separated in a materials recovery center so as to inventory the components which comprise the waste streams. Methods for making the engineered fuel feed stock described herein are also described.

Algorithms for engineering HHV fuels are disclosed in U.S. patent application Ser. No. 12/492,096, the contents of which are incorporated herein in its entirety. It has been determined that fuel feed stocks can be engineered so as to minimize harmful emissions by the addition of appropriate amounts of a sorbent. The fuel feed stock sulfur content ranges from between about 0.2 lb/MMBTUs to about 2.5 lbs/MMBTUs. These fuels, when combusted or gasified, produce emissions of less than 30 ppm by volume of SOx or chlorine pollutants if appropriate amounts of a sorbent is added. For instance, fuel feed stock can be engineered to have a coal-equivalent higher heating value of about 13,000 BTU/lb, and contain less than about 0.05% by weight, or 0.04 lbs/MMBTU of sulfur or chlorine. This engineered fuel feed stock, when combusted or gasified, would emit less than 30 ppm by volume of SOx or HCl without post treatment. These fuels have comparable energy density (BTU/lb) to coal, but without the problems of slagging, fusion and sulfur pollution, and can serve as a substitute for coal or a supplement to coal. Also, engineered fuel feed stocks can be designed, for example, to produce high quality syngas by optimizing the content of C, H, and O in the feed stock prior to gasification. Such engineered fuel feed stocks produce high quality syngas in terms of HHV if the syngas is to be used for power generation applications or $H_2/CO$ ratios, amounts of CO and $H_2$ present in the product syngas in the event that the syngas is to be used in chemical synthetic applications. Various waste stream components, including recyclable materials and recycling residue, and materials high in sulfur and chlorine content can now be used to produce the desired engineered fuel feed stock.

Accordingly, in one aspect, the present invention provides an engineered fuel feed stock, comprising a component derived from a processed MSW waste stream and a sorbent, the feed stock having a carbon content of between about 30% and about 80%, a hydrogen content of between about 3% and about 10%, and an ash content of less than about 10%. In some embodiments, the feed stock has a HHV of between about 3,000 BTU/lb and about 15,000 BTU/lb. In some embodiments, the feed stock has a volatile matter content of about 40% to about 80%. In some embodiments, the feed stock has a moisture content of less than about 30%. In some embodiments, the feed stock has a moisture content of between about 10% and about 30%. In other embodiments, the feed stock has a moisture content of between about 10% and about 20%. In still further embodiments, the feed stock has a moisture content of about 1% and about 10%. The engineered fuel feed stock contains substantially no glass, metal, grit and noncombustibles (other than those necessary to render the engineered fuel feed stock to be inert). In some embodiments, the sorbent is a calcium sorbent. In some embodiments the calcium sorbent is selected from limestone ($CaCO_3$), lime (CaO), hydrated lime ($Ca(OH)_2$, dolomite ($CaCO_3.MgO$). In some embodiments the calcium sorbent is from a non-renewable source. In some embodiments the calcium sorbent is derived from a mined material. In some embodiments the sorbent is from a renewable source. In some embodiments the sorbent comes from egg shells. In further embodiments, iron hydroxides, iron oxides are selected as sorbents. In some further embodiments some metal oxides such as zinc oxides, copper oxides, or nickel oxides, alone or in combination, can be selected as sorbents. In yet other embodiments, some waste materials which may be rich in one or more above mentioned elements, such as coal or wood ash, cement, iron filings, lime mud, can be used as sorbents. Further, materials such as pure carbon and charcoals from both wood and coal are all useful as sorbents because they create lower waste. Specifically, coal ash has higher alumina silicates which have additional sorbent capabilities. In other embodiments, the sorbent is a sodium sorbent. In other embodiments the sodium sorbent is sodium sesquicarbonate ("Trona").

In some embodiments, the sorbent is in an amount of between about 0.1% (weight sorbent/weight fuel feed stock (w/w)) and 50% (w/w). In other embodiments, the sorbent is in an amount of between about 1% (w/w) and 20% (w/w). In further embodiments, the sorbent is in an amount of between about 3% (w/w) and 15% (w/w). In still other embodiments, the sorbent is in an amount of between about 5% (w/w) and 10% (w/w). In some embodiments, the sorbent is in an amount that is determined by stoichiometry requirements for specific chemical reactions, based on which sulfur-derived or chlorine-derived pollutant is removed. In some embodiments, the sorbent is in an amount that is stoichiometrically about 10% to about 50% greater than the amount of sulfur-derived or chlorine-derived pollutant, or other pollutant to be removed. In some embodiments, the sorbent is in an amount that is stoichiometrically about 20% to about 40% greater than the amount of sulfur-derived or chlorine-derived pollutant, or other pollutant to be removed. In some embodiments, the sorbent is in an amount that is stoichiometrically about 30% greater than the amount of sulfur-derived or chlorine-derived pollutant, or other pollutant to be removed. In some embodiments, the sorbent is in an amount that is stoichiometrically about 10% to about 20% greater than the amount of sulfur-derived or chlorine-derived pollutant, or other pollutant to be removed. In further embodiments, two or more sorbents can be added with each in an amount as described above.

In some embodiments, when the engineered fuel feed stocks are used to co-gasify or co-combust with another fuel, such as coal, oil, natural gas, RDFs, other engineered fuel feed stock, or other suitable fuel, the amount of sorbents to be mixed with the engineered fuel feed stocks can be determined based on the total amount of sulfur-derived or chlorine-derived pollutant from both the engineered fuel feed stocks and the other fuel.

In some embodiments, the feed stock has a carbon content of between about 40% and about 70%. In some embodiments, the feed stock has a carbon content of between about 50% and about 60%. In some embodiments, the feed stock has a carbon content of between about 30% and about 40%. In some embodiments, the feed stock has a carbon content of between about 40% and about 50%. In some embodiments, the feed stock has a carbon content of between about 60% and about 70%. In some embodiments, the feed stock has a carbon content of between about 70% and about 80%. In some embodiments, the feed stock has a carbon content of about 35%. In some embodiments, the feed stock has a carbon content of about 45%. In some embodiments, the feed stock has a carbon content of about 55%. In some embodiments, the feed stock has a carbon content of about 65%. In some embodiments, the feed stock has a carbon content of about 75%.

In some embodiments, the feed stock has a hydrogen content of between about 4% and about 9%. In some embodiments, the feed stock has a hydrogen content of between about 5% and about 8%. In some embodiments, the feed stock has a hydrogen content of between about 6% and about 7%.

In some embodiments, the feed stock has a moisture content of between about 12% and about 28%. In some embodiments, the feed stock has moisture content of between about 14% and about 24%. In some embodiments, the feed stock has moisture content of between about 16% and about 22%. In some embodiments, the feed stock has moisture content of between about 18% and about 20%.

In some embodiments, the feed stock has an ash content of less than about 10%. In some embodiments, the feed stock has an ash content of less than about 9%. In some embodiments, the feed stock has an ash content of less than about 8%. In some embodiments, the feed stock has an ash content of less than about 7%. In some embodiments, the feed stock has an ash content of less than about 6%. In some embodiments, the feed stock has an ash content of less than about 5%. In some embodiments, the feed stock has an ash content of less than about 4%. In some embodiments, the feed stock has an ash content of less than about 3%.

In some embodiments, the feed stock has a HHV of between about 3,000 BTU/lb and about 15,000 BTU/lb. In some embodiments, the feed stock has a HHV of between about 4,000 BTU/lb and about 14,000 BTU/lb. In some embodiments, the feed stock has a HHV of between about 5,000 BTU/lb and about 13,000 BTU/lb. In some embodiments, the feed stock has a HHV of between about 6,000 BTU/lb and about 12,000 BTU/lb. In some embodiments, the feed stock has a HHV of between about 7,000 BTU/lb and about 11,000 BTU/lb. In some embodiments, the feed stock has a HHV of between about 8,000 BTU/lb and about 10,000 BTU/lb. In some embodiments, the feed stock has a HHV of about 9,000 BTU/lb.

In some embodiments, the feed stock has a volatile matter content of about 50% to about 70%. In some embodiments, the feed stock has a volatile matter content of about 60%.

In some embodiments, the engineered fuel feed stock has a ratio of H/C from about 0.025 to about 0.20. In some embodiments, the engineered fuel feed stock has a ratio of H/C from about 0.05 to about 0.18. In some embodiments, the engineered fuel feed stock has a ratio of H/C from about 0.07 to about 0.16. In some embodiments, the engineered fuel feed stock has a ratio of H/C from about 0.09 to about 0.14. In some embodiments, the engineered fuel feed stock has a ratio of H/C from about 0.10 to about 0.13. In some embodiments, the engineered fuel feed stock has a ratio of H/C from about 0.11 to about 0.12. In some embodiments, the engineered fuel feed stock has a ratio of H/C of about 0.13. In some embodiments, the engineered fuel feed stock has a ratio of H/C of about 0.08.

In some embodiments, the engineered fuel feed stock has an O/C ratio from about 0.01 to about 1.0. In some embodiments, the engineered fuel feed stock has an O/C ratio from about 0.1 to about 0.8. In some embodiments, the engineered fuel feed stock has an O/C ratio from about 0.2 to about 0.7. In some embodiments, the engineered fuel feed stock has an O/C ratio from about 0.3 to about 0.6. In some embodiments, the engineered fuel feed stock has an O/C ratio from about 0.4 to about 0.5. In some embodiments, the engineered fuel feed stock has an O/C ratio of about 0.9. In some embodiments, the engineered fuel feed stock has an O/C ratio of about 0.01.

In some embodiments, the engineered fuel feed stock upon gasification at 850° C. and an air equivalence ratio (ER) of 0.34 produces synthesis gas comprising $H_2$ in an amount from about 6 vol. % to about 30 vol. %; CO in an amount from about 14 vol. % to about 25 vol. %, $CH_4$ in an amount from about 0.3 vol. % to about 6.5 vol. %, $CO_2$ in an amount from about 6.5 vol. % to about 13.5% vol. %; and $N_2$ in an amount from about 44 vol. % to about 68 vol. %.

In some embodiments, the engineered fuel feed stock upon gasification at 850° C. and an ER of 0.34 produces synthesis gas having an $H_2$/CO ratio from about 0.3 to about 2.0. In some embodiments, the engineered fuel feed stock upon gasification at 850° C. and an ER of 0.34 produces synthesis gas having an $H_2$/CO ratio from about 0.5 to about 1.5. In some embodiments, the engineered fuel feed stock upon gasification at 850° C. and an ER of 0.34 produces synthesis gas having an $H_2/CO$ ratio from about 0.8 to about 1.2. In some embodiments, the engineered fuel feed stock upon gasification at 850° C. and an ER of 0.34 produces synthesis gas having an $H_2/CO$ ratio of about 1.0.

In some embodiments, the engineered fuel feed stock upon gasification at 850° C. and an ER of 0.34 produces synthesis gas having $H_2$ in an amount of about 20 vol. %; $N_2$ in an amount of about 46 vol. %; CO in an amount of about 25 vol. %; $CH_4$ in an amount of about 1 vol. %; $CO_2$ in an amount of about 8 vol. %; and a BTU/scf of about 160.

In some embodiments, the engineered fuel feed stock when combusted produces less harmful emissions as compared to the combustion of coal. In some embodiments, the engineered fuel feed stock when combusted produces less sulfur emission as compared to the combustion of coal. In some embodiments, the engineered fuel feed stock when combusted produces less HCl emission as compared to the combustion of coal. In some embodiments, the engineered fuel feed stock when combusted produces less heavy metal emissions such as for example mercury as compared to the combustion of coal. In some embodiments, the engineered fuel feed stock is designed to avoid the emission of particulate matters, NOx, CO, $CO_2$, volatile organic compounds (VOCs), and halogen gases.

In some embodiments, the engineered fuel feed stock is designed to have reduced emission profiles with respect to GHGs as compared to the GHGs emitted from combusted coal. In some embodiments, the engineered fuel feed stock is designed to have reduced emission profiles with respect to GHGs emitted from the combustion of biomasses such as for example, wood, switch grass and the like.

In some embodiments, the feed stock is in a loose, non-densified form. In other embodiments, the engineered fuel feed stock is in a densified form. In some embodiments, the densified form is a cube. In some embodiments, the densified form is rectangular. In other embodiments, the densified form is cylindrical. In some embodiments, the densified form is spherical. In some embodiments, the densified form is a briquette. In other embodiments, the densified form is a pellet. In some embodiments, the densified fuel is sliced into sheets of different thickness. In some embodiments, the thickness is between about 3/16 inches to about 3/4 inches. In some embodiments, the densified form is a honeycomb.

In some embodiments, the engineered fuel feed stock is rendered inert. In some embodiments, the engineered fuel feed stock comprises at least one additive that renders the feed stock inert. In some embodiments, an additive can be blended into the processed MSW waste stream that can render the resulting pellet inert. Some types of wet MSW contain a relatively high number of viable bacterial cells that can generate heat and hydrogen gas during fermentation under wet conditions, for example during prolonged storage or transportation. For example, an additive such as calcium hydroxide can be added to the MSW for the prevention of the rotting of food wastes and for the acceleration of drying of solid wastes. In some embodiments, the additive that renders the feed stock inert is CaO. Other non limiting examples of additives are calcium sulfoaluminate and other sulfate compounds, as long as they do not interfere with the downstream processes in which the engineered fuel feed stock is used.

Alternatively, the MSW can be rendered biologically inert through any known method for inactivating biological material. For example, X-rays can be used to deactivate the MSW before processing, or after processing. Drying can be used to remove the water necessary for organisms such as microbes to grow. Treatment of the MSW with high heat and optionally also high heat under pressure (autoclaving) will also render the MSW biologically inert. In one embodiment, the excess heat generated by the reciprocating engines or turbines fueled by the engineered pellets can be redirected through the system and used to render the MSW inert. In other embodiments, the feed stock is rendered inert through means such as microwave radiation.

In some embodiments, the densified form of the engineered fuel feed stock has a diameter of between about 0.25 inches to about 1.5 inches. In some embodiments, the densified form of the engineered fuel feed stock has a length of between about 0.5 inches to about 6 inches. In some embodiments, the densified form of the engineered fuel feed stock has a surface to volume ratio of between about 20:1 to about 3:1. In some embodiments, the densified form of the engineered fuel feed stock has a bulk density of about 10 $lb/ft^3$ to about 75 $lb/ft^3$. In some embodiments, the densified form of the engineered fuel feed stock has a porosity of between about 0.2 and about 0.6. In some embodiments, the densified form of the engineered fuel feed stock has an aspect ratio of between about 1 to about 10. In some embodiments, the densified form of the engineered fuel feed stock has a thermal conductivity of between about 0.023 BTU/(ft·hp·° F.) and about 0.578 BTU/(ft·hr·° F.). In some embodiments, the densified form of the engineered fuel feed stock has a specific heat capacity of between about $4.78 \times 10^{-5}$ BTU/(lb·° F.) to $4.78 \times 10^{-4}$ BTU/(lb·° F.). In some embodiments, the densified form of the engineered fuel feed stock has a thermal diffusivity of between about $1.08 \times 10^{-5}$ $ft^2/s$ to $2.16 \times 10^{-5}$ $ft^2/s$.

In some embodiments, the at least one waste material that enhances the gasification of the fuel feed stock is selected from fats, oils and grease (FOG). In some embodiments, the at least one waste material that enhances the gasification of the fuel feed stock is sludge. In some embodiments, the densified form of the engineered fuel feed stock is substantially encapsulated within the FOG component. In some of the embodiments, the encapsulation layer is scored. In still further embodiments, the scoring of the encapsulated densified form of the engineered fuel feed stock causes the fuel to devolatize more efficiently during gasification process than the fuel without the scoring.

In another aspect, an engineered fuel feed stock having a carbon content of between about 30% and about 80%, a hydrogen content of between about 3% and about 10%, a moisture content of between about 10% and about 30%, an ash content of less than about 10%, and a sorbent of between about 0.1% (w/w) and 50% (w/w) is described that is produced by a process comprising:
  a) receiving a plurality of MSW waste feeds at a material recovery facility;
  b) inventorying the components of the plurality of MSW waste feeds of step a) as they pass through a material recovery facility based on the chemical molecular characteristics of the components;
  c) comparing the chemical molecular characteristics of the components of the plurality of MSW waste feeds inventoried in step b) with the chemical molecular characteristics of the engineered fuel feed stock;
  d) adding a sorbent;
  e) optionally adding additional engineered fuel feed stock components which contain chemical molecular characteristics, whose sum together with the inventoried components of step b) equal the chemical molecular characteristics of the engineered fuel feed stock.

In some embodiments, the feed stock has a HHV of between about 3,000 BTU/lb and about 15,000 BTU/lb. In some embodiments, the feed stock has a volatile matter content of about 40% to about 80%. In some embodiments, the engineered fuel feed stock is reduced in size in order to homogenize the feed stock. In some embodiments, the engineered fuel feed stock is densified. In some embodiments, the densified feed stock is in the form of a briquette. In some embodiments, the densified feed stock is in the form of a pellet. In some embodiments, the densified feed stock is in the form of a cube.

In another aspect, an engineered fuel feed stock is described that is produced by a process comprising:
  a) separating a plurality of MSW waste feeds at a material recovery facility into a plurality of MSW waste components based on chemical molecular characteristics;
  b) selecting chemical molecular characteristics for the engineered fuel feed stock comprising a carbon content of between about 30% and about 80%, a hydrogen content of between about 3% and about 10%, a moisture content of between about 10% and about 30%, and an ash content of less than about 10%;
  c) selecting MSW waste components from step a) whose sum of chemical molecular characteristics equals the chemical molecular characteristics selected in step b);
  d) optionally adding other fuel components to the selections of step c) if the chemical molecular characteristics of the MSW waste components selected in step c) do not equal the chemical molecular characteristics of the selection of step b);
  e) selecting an amount of sorbent; and
  f) mixing the components of steps c) and e), and optionally of step d).

In some embodiments, the size of the mixture of step f) is reduced to help homogenize the engineered fuel feed stock. In some embodiments, a size and shape is determined for a densified form of the mixture of step f) or the size-reduced mixture of step e). In some embodiments, the mixture of step f) is densified. In other embodiments, the size-reduced mixture of step f) is densified. In some embodiments, the engineered fuel feed stock has a HHV of between about 3,000 BTU/lb and about 15,000 BTU/lb. In some embodiments, the feed stock has a volatile matter content of about 40% to about 80%.

In another aspect, a method of producing an engineered fuel feed stock from a processed MSW waste stream is described which comprises the steps of:
  a) selecting a plurality components from a processed MSW waste stream which components in combination have chemical molecular characteristics comprising a carbon content of between about 30% and about 80%, a hydrogen content of between about 3% and about 10%, a moisture content of between about 10% and about 30%, an ash content of less than 10%, and a sulfur content of less than 2%;
  b) combining and mixing together the selected components of step a) to form a feed stock;
  c) comparing the resulting chemical molecular characteristics of the feed stock of step b) with the chemical molecular characteristics of step a);
  d) optionally adding other fuel components to the selected components of step b) if the chemical molecular characteristics of the MSW waste components selected in step b) do not equal the chemical molecular characteristics of step a); and
  e) adding a sorbent.

In some embodiments, the size of the mixture of step b) or step d) is reduced to help homogenize the engineered fuel feed stock. In some embodiments, a size and shape is determined for a densified form of the mixture of step b) or the size-reduced mixtures of steps b) or d). In other embodiments, the size-reduced mixture of step e) is densified to a density of about 10 lbs/ft$^3$ to about 75 lbs/ft$^3$. In some embodiments, the engineered fuel feed stock has a HHV of between about 3,000 BTU/lb and about 15,000 BTU/lb. In some embodiments, the feed stock has a volatile matter content of about 40% to about 80%.

In another aspect, a method of producing a engineered fuel feed stock is described, the method comprising:
  a) receiving a plurality of MSW waste streams;
  b) selecting for the engineered fuel feed stock chemical molecular characteristics comprising a carbon content of between about 30% and about 80%, a hydrogen content of between about 3% and about 10%, a moisture content of between about 10% and about 30%, and an ash content of less than 10%;
  c) inventorying the components of the plurality of MSW waste streams based on the chemical molecular characteristics of the components;
  d) comparing the chemical molecular characteristics of the inventoried components of the plurality of MSW waste streams of step c) with the selected chemical molecular characteristics of step b);
  e) optionally adding additional fuel components with the required chemical molecular characteristics to inventoried components of step c) to meet the desired chemical molecular characteristics of step b) for the engineered fuel feed stock; and
  f) add a sorbent.

In some embodiments, the engineered fuel feed stock of steps c) or e) is mixed. In some embodiments, the engineered fuel feed stock of steps c) or e) is reduced in size. In some embodiments, the engineered fuel feed stock of steps c) or e) are densified. In some embodiments, the size-reduced engineered fuel feed stock of steps c) or e) are densified. In some embodiments, the engineered fuel feed stock is densified to about 10 lbs/ft$^3$ to about 75 lbs/ft$^3$.

In some embodiments, the engineered fuel feed stock is densified to form a briquette. In other embodiments, the engineered fuel feed stock is densified to form of a pellet.

It is a further object of the present invention to provide engineered fuel feed stocks comprising one or more sorbents that can be used to control a specific pollutant, or preferably a number of pollutants at the same time. In order to achieve multiple pollutant control, a multi-functional sorbent is ideally required; alternatively, multiple sorbents could be utilized with each sorbent being selected to treat for a particular element. Selection of sorbents is dependent on a various considerations, including, but not limited to, the following: (i) fuel characteristics, essentially what type and amount of the pollutants need to be controlled by sorbent(s); (ii) operating conditions, such as reducing or oxidizing environment, temperature, pressure, and conversion technologies (e.g., fixed bed, dense fluidized bed, circulating fluidized bed, etc.); (iii) reactivity of the sorbent and characteristics of the by-products, e.g., stability, melting point, boiling point, and toxicity; and (iv) economic effectiveness.

As described more fully below, a further object of the invention is to provide sorbent-integrated engineered fuel feed stocks with several distinct advantages, including, but not limited to, improved reaction kinetics, improved sorbent reactivity, improved pollutant removal efficiency, improved fuel conversion, improved corrosion control, reduced ash slagging, reduced operating temperature, extend power generating facility lifetime, avoid expensive retrofit costs, reduced operating and maintenance costs.

With sorbents embedded within the feed stock, an intimate contact between sorbent and pollutant can be achieved where they are generated. Compared to furnace injection in which the pollutant has migrated from within fuel particles to the bulk fuel or flue gas stream, the concentration of the pollutant is higher within the particles when the sorbent is part of the fuel. This configuration improves the reaction kinetics, thus enhancing the reaction.

Further, due to the temperature gradient across the fuel particles, sintering of sorbent inside the fuel particles is reduced, and thus sorbent reactivity is higher.

Combining the sorbent with feed stock to form an integrated fuel particle also allows the use of fine sorbent particles (e.g., <1 µm) while still achieving long residence time in the reaction chamber, which could be on the order of minutes, compared to only 1-2 seconds in case of furnace injection. Together, fine sorbent particles and long residence time would significantly increase the pollutant removal efficiency.

In cases where incompletely reacted sorbents may separate from the fuel particle and get into the flue gas stream, continuous reaction with $H_2S$ (or $SO_2$) in gas stream will continue. As a result, the sorbent utilization will be greatly improved.

Because the sorbent is part of the fuel feed stock, there is no need to have the sorbent handling systems that are normally required for dry sorbent injection systems (storage, delivery, atomizing, etc.).

Also, the products of the sorbent/pollutant reaction mostly remain in the bottom ash, the dust load on downstream dust collectors (i.e., electrostatic precipitator, baghouse, particulate matter scrubber) would be reduced, resulting savings in capital, operation and maintenance costs otherwise required for these devices.

For gasification, sorbent material can also catalytically improve the fuel conversion, and thus the gasification rate and performance can be enhanced (J. Weldon, G. B. Haldipur, D. A. Lewandowski, K. J. Smith, "Advanced coal gasification and desulfurization with calcium-based sorbent", KRW Energy Systems Inc., Madison, Pa. 15663.)

It is a further object of the present invention to provide an engineered fuel feed stock that controls heavy metal emissions.

It is a further object of the present invention to provide an engineered fuel feed stock that provides corrosion prevention or minimization.

It is a further object of the present invention to provide an engineered fuel feed stock that, improves operational performance, by, for example, reduction in slagging and/or improve fuel conversion especially for coal at low temperatures.

It is a further object of the present invention to provide an engineered fuel feed stock for co-firing with other fuels such as coal as a means to control emissions. This control is required because of the more and more stringent air emissions standards, for example EPA's new transport rule. (Proposed Transport Rule 75 FR 45210). The vast majority of coal-fired power plants in the U.S. will be forced by these rules into a critical decisions, i.e., either spending multi-million dollars to retrofit their emission control systems to meet compliance, or simply shutdown the power plant to avoid that expense. The use of engineered fuel feed stocks of the present invention will not only avoid the above retrofit cost, but would also allow the plant to extend its operational life., thereby avoiding costly retrofit upgrades for emission control and extending the useful life of an existing power generation plant that would not normally comply with stringent emission control regulations, such as the new EPA transport rule.

It is a further object of the present invention to provide an engineered fuel feed stock for co-firing with other waste fuel such as densified or loose RDF for both emission and corrosion control.

It is a further object of the present invention to provide an engineered fuel feed stock, comprising at least one component derived from a processed MSW waste stream and one or more sorbents selected from the group consisting of: sodium sesquicarbonate (Trona), sodium bicarbonate, sodium carbonate, zinc ferrite, zinc copper ferrite, zinc titanate, copper ferrite aluminate, copper aluminate, copper manganese oxide, nickel supported on alumina, zinc oxide, iron oxide, copper, copper oxide, limestone, lime, iron filings, Fe, FeO, $Fe_2O_3$, $Fe_3O_4$, $CaCO_3$, $Ca(OH)_2$, $CaCO_3.MgO$, soda, Trona, silica, alumina, china clay, kaolinite, bauxite, emathlite, attapulgite, coal ash, hydrated lime, dolomite, egg shells, and Ca-montmorillonite.

It is a further object of the present invention to provide an engineered fuel feed stock, comprising at least one component derived from a processed MSW waste stream, a calcium based sorbent, and a sodium based sorbent are combined according to the following to the following formula: the total moles of calcium in the sorbent plus the total moles of sodium in the sorbent divided by the total moles of sulfur present and the total moles of chlorine present.

It is a further object of the present invention to provide an engineered fuel feed stock, wherein the ratio is below 10. It is a further object of the present invention to provide an engineered fuel feed stock, wherein the ratio is below 5. It is a further object of the present invention to provide an engineered fuel feed stock, wherein the ratio is about 3. It is a further object of the present invention to provide an engineered fuel feed stock, wherein the ratio is about 2. It is a further object of the present invention to provide an engineered fuel feed stock, wherein the ratio is about 1.3. It is a further object of the present invention to provide an engineered fuel feed stock, comprising at least one component derived from a processed MSW waste stream and at least one sorbent in an amount calculated to mitigate the sulfur content of another fuel.

It is a further object of the present invention to provide an engineered fuel feed stock, comprising at least one component derived from a processed MSW waste stream and at least one sorbent in an amount calculated to reduce corrosion. It is a further object of the present invention to provide an engineered fuel feed stock that mitigates corrosion, where the corrosion is caused by sulfur. It is a further object of the present invention to provide an engineered fuel feed stock that mitigates corrosion, where the corrosion is caused by chlorine. It is a further object of the present invention to provide an engineered fuel feed stock that mitigates corrosion, where the corrosion is caused by sulfur compounds or by chlorine compounds.

It is an object of the present invention to provide an engineered fuel feed stock, comprising at least one component derived from processed MSW waste stream and at least one sorbent. It is a further object of the invention that the engineered fuel feed stock when converted produces less sulfur emissions as compared to the known level of sulfur emissions of at least one other fuel when converted. It is a further object of the invention that the engineered fuel feed stock when converted produces less chlorine emissions as compared the known level of chlorine emissions of at least one other fuel when converted. It is a further object of the invention that the engineered fuel feed stock when converted produces less heavy metal emissions as compared the known level of heavy metal emissions of at least one other fuel when converted. It is a further object of the invention that the engineered fuel feed stock when converted produces less emissions of particulate matter as compared to known levels of particulate matter emitted by of at least one other fuel when converted. It is a further object of the invention that the engineered fuel feed stock when converted produces less emissions of NOx, as compared to known levels of NOx emitted by of at least one other fuel when converted. It is a further object of the invention that the engineered fuel feed stock when converted produces less emissions of CO, as compared to known levels of CO emitted by of at least one other fuel when converted. It is a further object of the invention that the engineered fuel feed stock when converted produces less emissions of $CO_2$, as compared to known levels of $CO_2$ emitted by of at least one other fuel when converted. It is a further object of the invention that the engineered fuel feed stock when converted produces less emissions of volatile organic compounds (VOCs), as compared to known levels of VOCs emitted by of at least one other fuel when converted. It is a further object of the invention that the engineered fuel feed stock when converted produces less emissions of halogen gases as compared to known levels of halogen gases emitted by of at least one other fuel when converted. It is a further object of the invention that the engineered fuel feed stock when converted produces less GHG emissions as compared to the known level of GHG emitted from coal when converted.

An object of the invention is a method of generating energy comprising using an engineered fuel feed stock with at least one component derived from a processed MSW waste stream and at least one sorbent in a furnace. In a further object of the invention the energy is electricity. In a further object of the invention the energy is steam. In a further object of the invention the furnace is operated in a combustion mode. In a further object of the invention, the furnace is operated in a gasification mode. In a further object of the invention, other fuels are used in combination with the engineered fuel feed stock. In a further object of the invention the other fuel is a second engineered fuel feed stock comprising at least one component from a processed MSW waste stream and at least one sorbent. In a further object of the invention the first engineered fuel feed stock treats chlorine emissions and the second engineered fuel feed stock treats sulfur emissions. In a further object of the invention the other fuel is selected from the group consisting of oil, coal, biomass, loose RDF, and densified RDF. In a further object of the invention the engineered fuel feed stock controls all emissions. In a further object of the invention the engineered fuel feed stock controls corrosion. In a further object of the invention the engineered fuel feed stock maintains emissions below a government regulated requirement. In a further object of the invention the engineered fuel feed stock improves process performance. In a further object of the invention the improvement in process performance is reduced ash slagging. In a further object of the invention the improvement in process performance is higher efficiency. In a further object of the invention the improvement in process performance is increased conversion of fuel. In a further object of the invention, the improvement in process performance is reduced operating temperature. In a further object of the invention the improvement is extending the life of the furnace. In a further object of the invention the improvement is avoiding retrofit costs. In a further object of the invention the improvement is reduced operational costs. In a further object of the invention the improvement is reduced maintenance costs.

DETAILED DESCRIPTION OF THE INVENTION

Figure 1:
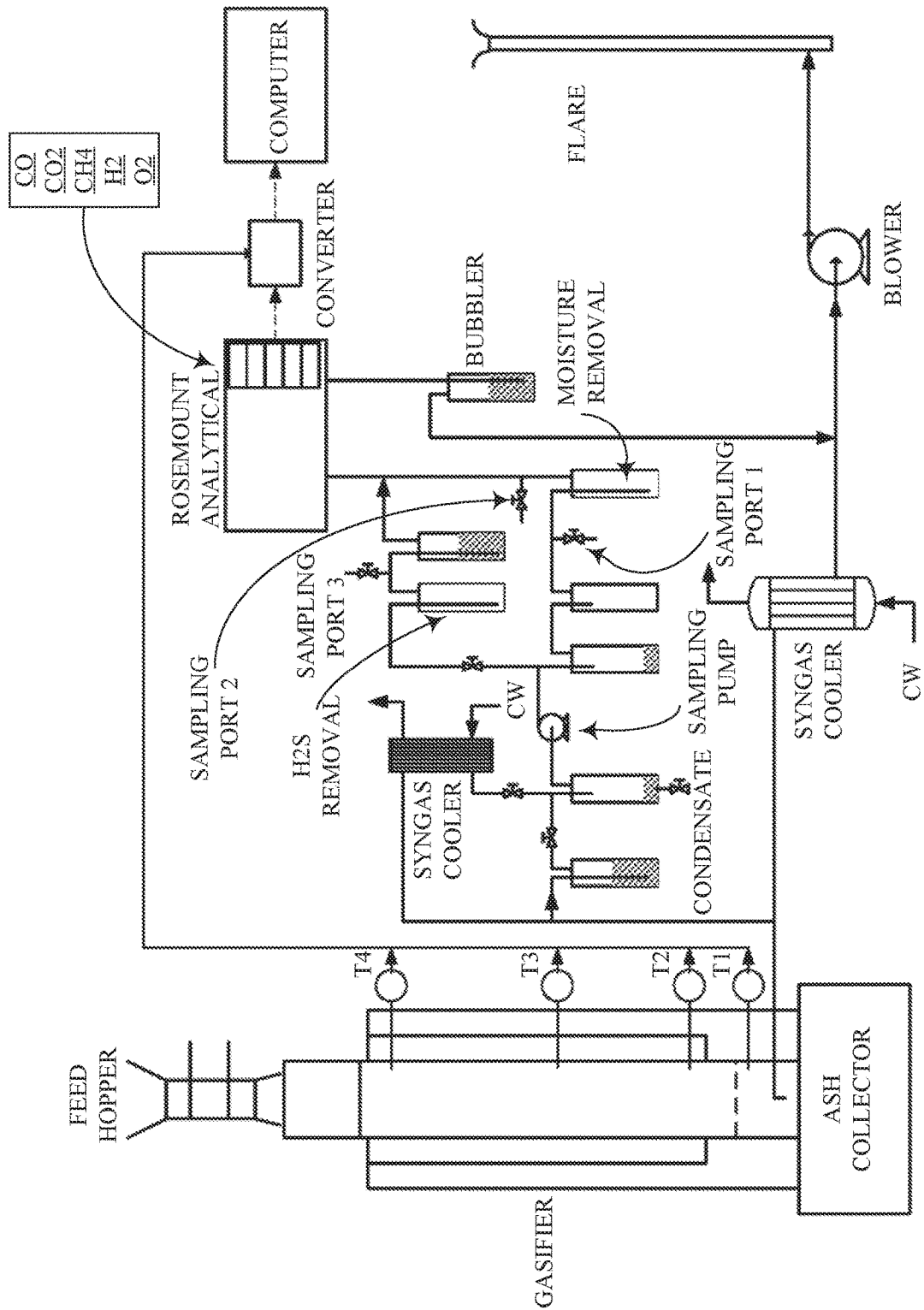
FIG. 1 discloses a schematic flow diagram of the gasification test system.

Novel engineered fuel feed stocks are provided that comprise at least one waste stream component derived from MSW, such as recycling residue which is the non-recoverable portion of recyclable materials, and a sorbent, which feed stocks are engineered to have predetermined chemical molecular characteristics. These feed stocks can possess the chemical molecular characteristics of biomass fuels such as, for example, wood and switch grass, and, can also have the positive characteristics of high BTU containing fuels such as, for example, coal, without the negative attributes of coal such as deleterious sulfur emissions. Also described are novel engineered fuel feed stocks that comprise chemical molecular characteristics not observed in natural fuels such as, for example, biomass, coal, or petroleum fuels. These novel fuels contain, for example, unique ratios of carbon, hydrogen, and ash, such that, when compared to known fuels, provide a superior combustion or gasification profile. Because these novel feed stocks have superior combustion or gasification profiles, they provide novel fuels for many different types of combustors and gasifiers which, while functioning adequately due to the uniformity of the natural fuel, do not function optimally due to the less than optimized chemical molecular characteristics of natural fuels. Engineered fuel feed stocks such as those useful for the production of thermal energy, power, biofuels, petroleum, and chemicals can be engineered and synthesized and which upon combustion or gasification do not produce deleterious amounts of sulfur or chlorine pollutants.

The engineered fuel feed stock described herein provides an efficient way to use a broader range of fuel sources from waste such as rubber, carpet and certain plastics, such as, for example, PVC that otherwise are avoided due to the production of significant amounts of sulfur and chlorine containing pollutants.

The following specification describes the invention in greater detail.

Definitions

The term "air equivalence ratio" (ER) means the ratio of the amount of air supplied to the gasifier divided by the amount of air required for complete fuel combustion. Air equivalence ratio, "ER," can be represented by the following equation:

$$ER = \frac{\text{Air supplied to the gasifier}}{\text{Air required for complete fuel combustion}}$$

The term "British Thermal Unit" (BTU) means the amount of heat energy needed to raise the temperature of one pound of water by one degree F.

The term "carbon boundary" means the temperature obtained when exactly enough oxygen is added to achieve complete gasification, or carbon conversion. Above this temperature there is no solid carbon present.

The term "carbon content" means all carbon contained in the fixed carbon (see definition below) as well as in all the volatile matters in the feed stock.

The term "carbon conversion" means to convert solid carbon in fuel feed stock into carbon-containing gases, such as $CO$, $CO_2$ and $CH_4$ in most gasification operations The term "commercial waste" means solid waste generated by stores, offices, restaurants, warehouses, and other non-manufacturing, non-processing activities. Commercial waste does not include household, process, industrial or special wastes.

The term "construction and demolition debris" (C&D) means uncontaminated solid waste resulting from the construction, remodeling, repair and demolition of utilities, structures and roads; and uncontaminated solid waste resulting from land clearing. Such waste includes, but is not limited to bricks, concrete and other masonry materials, soil, rock, wood (including painted, treated and coated wood and wood products), land clearing debris, wall coverings, plaster, drywall, plumbing fixtures, non-asbestos insulation, roofing shingles and other roof coverings, asphaltic pavement, glass, plastics that are not sealed in a manner that conceals other wastes, empty buckets ten gallons or less in size and having no more than one inch of residue remaining on the bottom, electrical wiring and components containing no hazardous liquids, and pipe and metals that are incidental to any of the above. Solid waste that is not C&D debris (even if resulting from the construction, remodeling, repair and demolition of utilities, structures and roads and land clearing) includes, but is not limited to asbestos waste, garbage, corrugated container board, electrical fixtures containing hazardous liquids such as fluorescent light ballasts or transformers, fluorescent lights, carpeting, furniture, appliances, tires, drums, containers greater than ten gallons in size, any containers having more than one inch of residue remaining on the bottom and fuel tanks. Specifically excluded from the definition of construction and demolition debris is solid waste (including what otherwise would be construction and demolition debris) resulting from any processing technique, that renders individual waste components unrecognizable, such as pulverizing or shredding.

The term "devolatization" means a process that removes the volatile material in a engineered fuel feed stock thus increasing the relative amount of carbon in the engineered fuel feed stock.

The term "fixed carbon" is the balance of material after moisture, ash, volatile mater determined by proximate analysis.

The term "garbage" means putrescible solid waste including animal and vegetable waste resulting from the handling, storage, sale, preparation, cooking or serving of foods. Garbage originates primarily in home kitchens, stores, markets, restaurants and other places where food is stored, prepared or served.

The term "gasification" means a technology that uses a noncombustion thermal process to convert solid waste to a clean burning fuel for the purpose of generating for example, electricity, liquid fuels, and diesel distillates. Noncombustion means the use of no air or oxygen or substoichiometric amounts of oxygen in the thermal process.

The term "hazardous waste" means solid waste that exhibits one of the four characteristics of a hazardous waste (reactivity, corrosivity, ignitability, and/or toxicity) or is specifically designated as such by the EPA as specified in 40 CFR part 262.

The term "Heating Value" is defined as the amount of energy released when a fuel is burned completely in a steady-flow process and the products are returned to the state of the reactants. The heating value is dependent on the phase of water in the combustion products. If $H_2O$ is in liquid form, heating value is called HHV (Higher Heating Value). When $H_2O$ is in vapor form, heating value is called LHV (Lower Heating Value).

The term "higher heating value" (HHV) means the caloric value released with complete fuel combustion with product water in liquid state. On a moisture free basis, the HHV of any fuel can be calculated using the following equation:

$$HHV_{Fuel} = 146.58C + 568.78H + 29.4S - 6.58A - 51.53(O+N).$$

wherein C, H, S, A, O and N are carbon content, hydrogen content, sulfur content, ash content, oxygen content and nitrogen content, respectively, all in weight percentage.

The term "municipal solid waste" (MSW) means solid waste generated at residences, commercial or industrial establishments, and institutions, and includes all processable wastes along with all components of construction and demolition debris that are processable, but excluding hazardous waste, automobile scrap and other motor vehicle waste, infectious waste, asbestos waste, contaminated soil and other absorbent media and ash other than ash from household stoves. Used tires are excluded from the definition of MSW. Components of municipal solid waste include without limitation plastics, fibers, paper, yard waste, rubber, leather, wood, and also recycling residue, a residual component containing the non-recoverable portion of recyclable materials remaining after municipal solid waste has been processed with a plurality of components being sorted from the municipal solid waste.

The term "nonprocessable waste" (also known as noncombustible waste) means waste that does not readily gasify in gasification systems and does not give off any meaningful contribution of carbon or hydrogen into the synthesis gas generated during gasification. Nonprocessable wastes include but are not limited to: batteries, such as dry cell batteries, mercury batteries and vehicle batteries; refrigerators; stoves; freezers; washers; dryers; bedsprings; vehicle frame parts; crankcases; transmissions; engines; lawn mowers; snow blowers; bicycles; file cabinets; air conditioners; hot water heaters; water storage tanks; water softeners; furnaces; oil storage tanks; metal furniture; propane tanks; and yard waste.

The term "processed MSW waste stream" means that MSW has been processed at, for example, a materials recovery facility, by having been sorted according to types of MSW components. Types of MSW components include, but are not limited to, plastics, fibers, paper, yard waste, rubber, leather, wood, and also recycling residue, a residual component containing the non-recoverable portion of recyclable materials remaining after municipal solid waste has been processed with a plurality of components being sorted from the municipal solid waste. Processed MSW contains substantially no glass, metals, grit, or non-combustibles. Grit includes dirt, dust, granular wastes such as coffee grounds and sand, and as such the processed MSW contains substantially no coffee grounds.

The term "processable waste" means wastes that readily gasify in gasification systems and give off meaningful contribution of carbon or hydrogen into the synthesis gas generated during gasification. Processable waste includes, but is not limited to, newspaper, junk mail, corrugated cardboard, office paper, magazines, books, paperboard, other paper, rubber, textiles, and leather from residential, commercial, and institutional sources only, wood, food wastes, and other combustible portions of the MSW stream.

The term "pyrolysis" means a process using applied heat in an oxygen-deficient or oxygen-free environment for chemical decomposition of solid waste.

The term "recycling residue" means the residue remaining after a recycling facility has processed its recyclables from incoming waste which no longer contains economic value from a recycling point of view.

The term "sludge" means any solid, semisolid, or liquid generated from a municipal, commercial, or industrial wastewater treatment plant or process, water supply treatment plant, air pollution control facility or any other such waste having similar characteristics and effects.

The term "solid waste" means unwanted or discarded solid material with insufficient liquid content to be free flowing, including, but not limited to rubbish, garbage, scrap materials, junk, refuse, inert fill material, and landscape refuse, but does not include hazardous waste, biomedical waste, septic tank sludge, or agricultural wastes, but does not include animal manure and absorbent bedding used for soil enrichment or solid or dissolved materials in industrial discharges. The fact that a solid waste, or constituent of the waste, may have value, be beneficially used, have other use, or be sold or exchanged, does not exclude it from this definition.

The term "sorbent" means a material added to the engineered fuel feed stock that either acts as a traditional sorbent and adsorbs a chemical or elemental by-product, or reacts with a chemical or elemental by-product, or in other cases, simply as an additive to alter the fuel feed stock characteristics such as ash fusion temperature.

The term "steam/carbon ratio" (S/C) means the ratio of total moles of steam injected into the gasifier/combustor divided by the total moles of carbon feed stock. The steam/carbon ratio, "S/C," can be represented by the following equation:

$$S/C = \frac{\text{Total moles of steam}}{\text{Total moles of carbon in feed stock}}$$

The term "thermal efficiency" (also known as cold gas efficiency) means the ratio of the total HHV contained in the resulting product gas divided by the total HHV that was contained in the fuel input. Thermal efficacy, "Eff," can be represented by the following equation:

$$Eff = \frac{\text{Total } HHV \text{ of synthesis gas}}{\text{Total } HHV \text{ of fuel input}} \times 100\%$$

The term "volatile materials" (also known as volatile organic compounds) means the organic chemical compounds that have high enough vapor pressures under normal conditions to significantly vaporize and enter the atmosphere. Non-limiting examples of volatile materials include aldehydes, ketones, methane, and other light hydrocarbons.

Described herein are novel engineered fuel feed stocks comprising at least one component derived from a processed MSW waste stream and a sorbent, the feed stocks having any of a number of desired chemical molecular characteristics, including, but not limited to carbon content, hydrogen content, oxygen content, nitrogen content, ash content, moisture content, and HHV content. This feed stock is useful for a variety of chemical conversion processes, used alone or with other fuels together. Also described are processes for producing an engineered fuel feed stock and methods of making same.

One abundant source of engineered fuel feed stock is MSW. MSW is solid waste generated at residences, commercial or industrial establishments, and institutions, and includes all processable wastes along with all components of construction and demolition debris that are processable, but excluding hazardous waste, automobile scrap and other motor vehicle waste, infectious waste, asbestos waste, contaminated soil and other absorbent media and ash other than ash from household stoves. It does include garbage, refuse, and other discarded materials that result from residential, commercial, industrial, and community activities. The composition of MSW varies widely depending on time of collection, season of the year of collection, the types of customers from which the MSW is collected on any given day, etc. MSW may contain a very wide variety of waste or discarded material. For instance, the waste may include biodegradable waste, non-biodegradable waste, ferrous materials, non-ferrous metals, paper or cardboard in a wide variety of forms, a wide range of plastics (some of which may contain traces of toxic metals used as catalysts, stabilizers or other additives), paints, varnishes and solvents, fabrics, wood products, glass, chemicals including medicines, pesticides and the like, solid waste of various types and a wide range of other materials. The waste includes household waste and industrial waste. Industrial waste contemplated for use herein is low in toxic or hazardous materials. However, MSW is processed in order to remove non-processable components prior to engineering the engineered fuel feed stocks described herein.

Processed MSW has been sorted or inventoried according to types of MSW components. Types of MSW components include, but are not limited to, plastics, fibers, paper, yard waste, rubber, leather, wood, and also recycling residue, a residual component containing the non-recoverable portion of recyclable materials remaining after municipal solid waste has been processed with a plurality of components being sorted from the municipal solid waste. Processed MSW contains substantially no glass, metals, grit, or non-combustibles. Grit includes dirt, dust, granular wastes such as coffee grounds and sand, and as such the processed MSW contains substantially no coffee grounds. The term "substantially no" as used herein means that no more than 0.01% of the material is present in the MSW components.

Another fuel source for use in an engineered fuel feed stock is FOGs. FOGs are commonly found in such things as meats, sauces, gravy, dressings, deep-fried foods, baked goods, cheeses, butter and the like. Many different businesses generate FOG wastes by processing or serving food, including; eating and drinking establishments, caterers, hospitals, nursing homes, day care centers, schools and grocery stores. FOGs have been a major problem for municipalities. Studies have concluded that FOGs are one of the primary causes of sanitary sewer blockages which result in sanitary sewer system overflows (SSOs) from sewer collection systems. These SSOs have caused numerous problems in some municipalities including overflow out of the sewage lines out of maintenance (manhole) holes and into storm drains. The water in storm drains flows into the water ways and eventually into the ocean. SSOs pose a threat to public health, adversely affect aquatic life, and are expensive to clean up. The most prevalent cause of the SSOs is FOG accumulation in the small to medium sewer lines serving food service establishments. Thus, a use as fuel would provide a means of disposal of FOGs without the prevalence of SSOs occurring due to the discharge of FOGs into the waste water.

Present methods of discarding FOGs, besides directly into the sewer systems, include landfills. While these types of wastes are generally considered nuisances, they contain a high carbon content and hydrogen content, essentially no ash, sulfur and chlorine that can be transformed into a quality source of fuel.

Other types of oils and greases useful in the present invention are petroleum waste products. Non-limiting examples of petroleum waste products include discarded engine oil.

Yet another type of waste useful in the production of engineered fuel feed stock is biomass waste, also known as biogenic waste. Biomass refers to living and recently dead biological material that can be used as fuel or for industrial production. Most commonly, biomass refers to plant matter grown for use as biofuel, but it also includes plant or animal matter used for production of fibers, chemicals or heat. Biomass may also include biodegradable wastes that can be burnt as fuel. It excludes organic material which has been transformed by geological processes into substances such as coal or petroleum. Non-limiting types of biomass waste include woods, yard wastes, plants, including miscanthus, switch grass, hemp, corn, poplar, willow, sugarcane and oil palm (palm oil), coconut shells, and shells of nuts.

A distinctive feature of biomass is that it contains carbon-14, which is ubiquitous in all living things. Carbon-14 slowly and gradually decays once a living organism dies. After 50,000 years, all the carbon-14 has decayed. Therefore, fossil fuels like coal, natural gas, and oil have no carbon-14. By testing the carbon-14, one can show what fraction of the given fuel, or MSW, is biogenic. This information is important because it allows the plant operator to account for the amount of material that is fired in the furnace that is derived from a renewable biomass. Moreover, it allows the regulators to directly measure the amount of carbon that is attributed from the biomass and the amount that is from a fossil fuel source. It also allows the operator to directly calculate the amount of renewable fuel used in the generation of energy to be able to sell or exchange those carbon offsets. The engineered fuel feed stock disclosed in this invention has the ability to adjust the fraction of biomass in order to achieve a desired target of biogenic carbon, which provides the users of the engineered fuel feed stock a quantitative measure as they claim any renewable energy credits.

Yet another type of waste useful in the production of engineered fuel feed stock is sludge. Sludge is a mixture of solid wastes and bacteria removed from the wastewater at various stages of the treatment process. It can be categorized as "primary sludge" and "secondary sludge". Primary sludge is about 4% solids and 96% water. It consists of the material which settles out of wastewater in the primary sedimentation tanks, before bacterial digestion takes place. Secondary or activated sludge is much more liquid—about 1% solids and 99% water. Secondary sludge consists of bacteria and organic materials on which the bacteria feed. About 30% of the secondary sludge produced is returned to the aeration tanks to assist with the biological process of sewage treatment. The remaining 70% must be disposed of.

The sludge contemplated for use in the present invention is municipal sludge a.k.a. biosolids. Municipal sludge does not include papermill or other industrial/agricultural sludge. The key determinants of the caloric or BTU value of a sludge are its dryness expressed as Total Solids or TS on a wet weight basis (or inversely as water content) and its volatile solids content (Total Volatile Solids or TVS expressed on a dry weight basis). There are two distinct types of sludge—1) raw sludge (sludge treated only with primary and secondary aerobic clarifiers) and 2) digested sludge (add anaerobic digestion to number 1). Anaerobic sludge is typically 60% TVS and raw sludge is typically 75-80% TVS. The TS of sludge cake (dewatered sludge) varies depending on the method used by the treatment plant to dewater the sludge, and ranges from 10% to 97+%. One pound of Volatile Solids has about 10,000-12,000 BTU, e.g., it requires about 1,200 BTU to drive off 1 lb of water as steam.

Other types of materials useful in the production of engineered feed stocks described herein are animal wastes such as manures, animal biomass (meat and bone tissue), poultry litter, fossil fuels such as coal, coal by products, petroleum coke, black liquor, and carbon black.

Any type of sorbent that adsorbs deleterious gases can be used in the present invention. Both sodium-based sorbents as well as calcium-based sorbents are useful. Non-limiting examples of sodium-based sorbents include sodium sesquicarbonate (Trona), sodium bicarbonate, and sodium carbonate. Non-limiting examples of calcium-based sorbents include calcium carbonate ($CaCO_3$), lime (CaO), hydrated lime ($Ca(OH)_2$, and dolomite ($CaCO_3.MgO$). These sorbents can be obtained from renewable sources, such as egg shells, or they can be obtained from non-renewable sources like mines.

Further examples of sorbents useful in the present invention include, but are not limited to, sodium sesquicarbonate (Trona), sodium bicarbonate, sodium carbonate, zinc ferrite, zinc copper ferrite, zinc titanate, copper ferrite aluminate, copper aluminate, copper manganese oxide, nickel supported on alumina, zinc oxide, iron oxide, copper, copper (I) oxide, copper (II) oxide, limestone, lime, Fe, FeO, $Fe_2O_3$, $Fe_3O_4$, iron filings, $CaCO_3$, $Ca(OH)_2$, $CaCO_3.MgO$, silica, alumina, china clay, kaolinite, bauxite, emathlite, attapulgite, coal ash, egg shells, and Ca-montmorillonite.

The amount of sorbent useful in the invention is determined based on the amount of sulfur-containing fuel or chlorine-containing fuel in the engineered feed stock, and in case of co-gasifying or co-firing with another fuel, the total amount of sulfur-containing fuel or chlorine-containing fuel in both the engineered feed stock and the other fuel. For example, if the amount of sulfur or chlorine is below 1% (w/w), then 4.5% (w/w) of sorbent is required for no more than 0.1% of sulfur pollutants or chlorine pollutants to be produced during combustion or gasification.

Methods of Making

The engineered fuel feed stock described herein comprises at least one component derived from a processed MSW waste stream and a sorbent and can be made by any process known to those of skill in the art. In particular, the processes described in U.S. patent application Ser. No. 12/492,096, the contents of which are incorporated herein by reference in its entirety, can be used to make a variety of fuel feed stocks that do not contain a sorbent. U.S. patent application Ser. No. 12/492,096 describes fuel feed stocks comprised of at least one component derived from a processed MSW waste stream, the feed stock having less than 2% sulfur and less than 1% chlorine, respectively. In the present invention, amounts of sulfur and chlorine may be higher in the engineered fuel feed stock than those described in U.S. patent application Ser. No. 12/492,096 due to the presence of the sorbent which counteracts the production of sulfur and chlorine pollutants during the combustion or gasification process. Different characteristics for the target fuel feed stock are described in U.S. patent application Ser. No. 12/492,096 and can be achieved by following the processes as described therein. For example, engineered fuel feed stocks having different amounts of C, H, O, HHV, sulfur, chlorine, as well as ash content and moisture content are described. Also described are different sizes of compressed forms of final fuel feed stock as well as how to calculate optimal dimensions of same for gasification or combustion.

Figure 6:
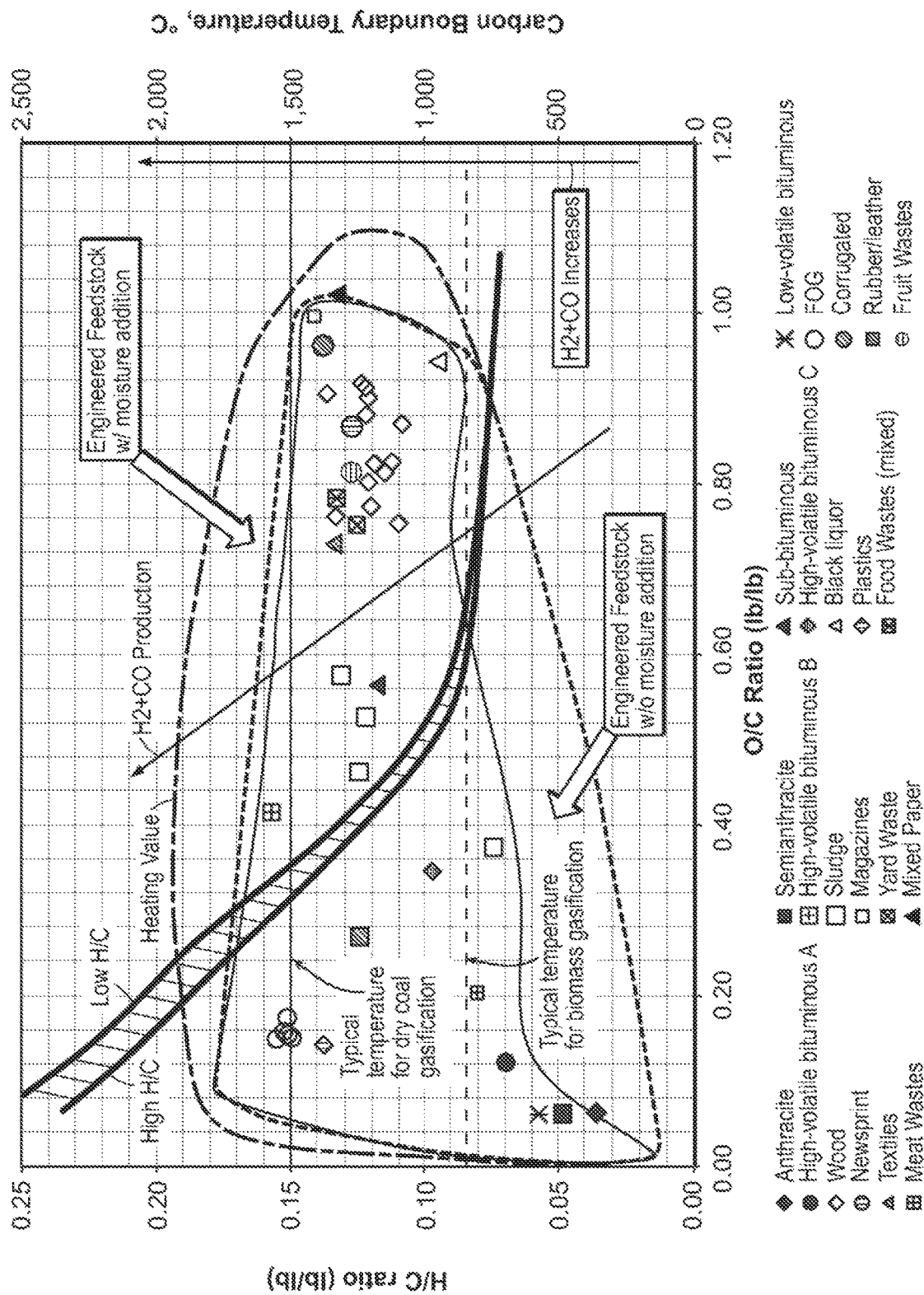
FIG. 6 shows commonly available feed stock materials, such as, for example, coal, FOGs, wood, sludge, black liquor, rubber and MSW streams, positioned in terms of their hydrogen content to carbon content ratio (H/C) (lb/lb) and oxygen content to carbon content (O/C) (lb/lb) ratio.

FIG. 6 shows commonly available feed stock materials, such as, for example, coal, FOGs, wood, sludge, black liquor, rubber and MSW streams, positioned in terms of their hydrogen content to carbon content ratio (H/C) (lb/lb) and oxygen content to carbon content (O/C) (lb/lb) ratio. When these natural feed stocks are surrounded on the graph by a solid line, an envelope is formed, which indicates the range of H/C and O/C for naturally occurring materials. FIG. 1 also plotted the carbon boundary temperature against the O/C ratio, with variations with H/C indicated by a slashed area. The carbon boundary temperature is the temperature obtained when exactly enough oxygen is added to achieve complete carbon conversion. For biomass gasification the typical temperature is about 850° C. and for dry coal gasification the typical temperature is about 1,500° C. Fuels such as anthracite, semianthracite, high- and low-volatile bituminous all have low H/C ratios from about 0.03 to 0.07 and low O/C content ratios from about 0.05 to about 0.12. These fuels require high temperatures due to the low O/C ratio and normally require steam injection to promote complete conversion of the carbon during gasification. Other feed stocks such as various woods, magazines, mixed paper, and corrugated cardboard all have relatively high H/C content ratios of about 0.1 to about 0.14 and O/C content ratios of about 0.8 to about 1.0, which in practice require low gasification temperatures. For feed stocks to be fully gasified at about 850° C., it is seen from FIG. 1 that the O/C ratio in feed stock should be about 0.55 to 0.6. For woody biomass feed stocks which have a O/C ratio of about 0.75 to 0.90, over-oxidizing (or increased oxidation) may occur at this temperature, and thus a higher $CO_2$ in the syngas would be expected. Therefore, it is an advantage of the engineered feed stock that fuel O/C and H/C ratios can be adjusted to allow for optimal gasification operation and performance to be achieved.

The amount of sorbent useful in the invention is determined based on the amount of sulfur- and/or chlorine-containing fuel in the engineered feed stock, and in case of co-gasifying or co-firing with another fuel, the total amount of sulfur-containing fuel or chlorine-containing fuel in both the engineered feed stock and the other fuel. For example, if the amount of sulfur is below 2%, then 8% (w/w) of sorbent is required for no more than 0.4% of sulfur pollutants or chlorine pollutants to be produced during thermoconversion. If the $SO_2$ emission limit for a facility is set at 0.5 lbs/MMBtu, this limit can be met, for example, if the feed stock has a sulfur content of less than 0.25%. The feed stocks described herein would help certain states avoid the need for installing expensive $SO_2$ control devices.

The MSW can be processed by any method that allows for identification and separation of the component parts according to material type, such as by plastics, fibers, textiles, paper in all its forms, cardboard, rubber, yard waste, food waste, and leather. Methods of separation such as those disclosed in U.S. Pat. No. 7,431,156 and U.S. Patent Application Publication Nos. 2006/0254957, 2008/0290006, and 2008/0237093, the disclosures of which are hereby incorporated in their entirety, can be used for separating the components of waste.

The MSW can also be processed by any method that allows for identification and separation of the component parts according to their chemical characterisitcs, and sorted and stored broadly into two, three, four or five classes. Methods of separation such as those disclosed in U.S. Patent Application Publication No. 2010/0018113, the disclosures of which are hereby incorporated in their entirety, can be used for separating the components of waste.

It is understood that modifications may be made to the methods of separation disclosed above that allow for the recovery of the individual components of MSW for use in engineering engineered fuel feed stock as described herein.

In some embodiments, the component or components of the engineered feed stock are mixed. In some of the embodiments, the mixed components are reduced in size using known techniques such as shredding, grinding, crumbling and the like. Methods for the reduction in size of MSW components is well known and for example are described in U.S. Pat. No. 5,888,256, the disclosure of which is incorporated by reference in its entirety. In other embodiments, the individual components are first reduced in size prior to mixing with other components. In some embodiments, the mixed components of the engineered fuel feed stock are densified using known densification methods such as, for example, those described in U.S. Pat. No. 5,916,826, the disclosure of which is incorporated by reference in its entirety. In some embodiments, the densification forms pellets by the use of a pelletizer, such as a Pasadena hand press, capable of exerting up to 40,000 force-pounds. In some other embodiments, the densification can be in other forms including briquettes, cubes, rectangular-shaped, cylindrical-shaped, spherical-shaped, honeycomb or sliced into sheets of different thickness. One of ordinary skill would recognize that this list is for illustrative purposes and other densification shapes are possible and contemplated within the scope of this invention.

In some embodiments, the FOGS component is added directly to the mixing tank. In other embodiments, the FOGS component is added after mixing just before the waste is placed into a pelletizing die.

By use of a pelletizer under appropriate conditions, pellets are produced having a range of dimensions. The pellets should have a diameter of at least about 0.25 inch, and especially in the range of about 0.25 inches to about 1.5 inches. The pellets should have a length of at least about 0.5 inch, and especially in the range of about 0.5 inches to about 6 inches.

By selection of the appropriate die to be used with the pelletizer, the pellets become scored on the surface of the encapsulation. This scoring may act as an identifying mark. The scoring can also affect the devolatization process such that the scored pellets volatize at a more efficient rate than the unscored pellets.

In some embodiments, the engineered fuel feed stock described herein is biologically, chemically and toxicologically inert. The terms biologically inert, chemically inert, and toxicologically inert mean that the engineered fuel feed stock described herein does not exceed the EPA's limits for acceptable limits on biological, chemical and toxicological agents contained within the engineered fuel feed stock. The terms also include the meaning that the engineered fuel feed stock does not release toxic products after production or upon prolonged storage. The engineered fuel feed stock does not contain, for example pathogens or live organisms, nor contain the conditions that would promote the growth of organisms after production or upon prolonged storage. For example, the engineered fuel feed stock in any form described herein can be designed so as to have a moisture content sufficient so as not to promote growth of organisms. The engineered fuel feed stock can be designed to be anti-absorbent, meaning it will not absorb water to any appreciable amount after production and upon prolonged storage. The engineered fuel feed stock is also air stable, meaning it will not decompose in the presence of air to give off appreciable amounts of volatile organic compounds. The engineered fuel feed stock described herein may be tested according to known methods in order to determine whether they meet the limits allowed for the definition of inert. For example, 40 CFR Parts 239 through 259 promulgated under Title 40—Protection of the Environment, contains all of the EPA's regulations governing the regulations for solid waste. The EPA publication SW-846, entitled Test Methods for Evaluating Solid Waste, Physical/Chemical Methods, is OSW's official compendium of analytical and sampling methods that have been evaluated and approved for use in complying with 40 CFR Parts 239 through 259, in relation to solid waste, which is incorporated by reference herein in its entirety.

Fuel Characteristics can Affect the Feed Stock Composition

Often more than one pollutant present in the fuel needs to be controlled, and there can be a considerable difference in reactivity among pollutants, which one common sorbent can not often handle. In these cases, multi-sorbents are ideal.

For coal gasification and combustion, sulfur is the most dominant constituent (in 0.5-5 wt. %) while the chlorine content is much less (~0.1 wt. %). A common sorbent that can effectively remove sulfur, but that can also remove some chlorine, is preferred. One group of this type of sorbent includes calcium-based sorbents, e.g., calcium carbonate ($CaCO_3$), lime (CaO), hydrated lime ($Ca(OH)_2$), dolomite ($CaCO_3.MgO$), which can be used to capture both sulfur (predominantly $H_2S$ in gasification and $SO_2$ in combustion) and chlorine (predominantly HCl).

For biomass gasification and combustion, because sulfur is generally lower (i.e., typically 0.2-0.5 wt. %) and chlorine is higher (i.e., typically >0.5 wt. %), calcium or sodium-based sorbents can be used. In gasification conditions, if CaO is used as the sorbent, it would react with $H_2S$ to produce CaS and with HCl to $CaCl_2$, but CaS could also react with $HCl(CaS+2HCl<=>CaCl_2+H_2S)$ to re-produce $H_2S$. Therefore, sodium-based sorbents (e.g., nahcolite: $NaHCO_3$, soda/Trona: $NaHCO_3.Na_2CO_3$) are used in preferred embodiments (also the product NaCl has a higher melting temperature 801° C. versus 772° C. of $CaCl_2$). However, because CaS has a melting temperature of 2,525° C., it may be beneficial to use both calcium- and sodium-based sorbents in an appropriate proportion so that some of $H_2S$ would be converted by calcium-based sorbent to CaS, and HCl by sodium-based sorbent to NaCl, and as a result, the produced ash would have an increased melting temperature so ash slagging or agglomeration would be reduced.

Also with biomass fuels, the high concentration of alkali metals (e.g., potassium (K)) adds an additional pollutant load that must be mitigated by the sorbent. As effective sorbents to retain alkali metals, and some of the trace metals, silica, alumina, and aluminum silicates such as china clay, kaolinite, bauxite, emathlite, attapulgite, Ca-montmorillonite, iron oxide, calcium oxide and limestone are all reported to be capable of retain alkali and other trace metals. Coal ashes that are rich in silica and alumina are also useful as additives in this case. These reactions retain the most corrosive alkali chloride salts (AlkCl) but liberate HCl as shown below:

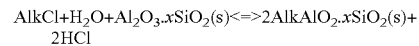

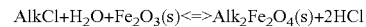

The produced salts have higher melting temperature, and thus prevent chloride salts corrosion of heat transfer surfaces.

The presence of halogens, most importantly chlorine is a very important factor to be taken into consideration when designing a feed stock of the present invention. As discussed above, waste materials are often used as fuel, and the amount of chlorine present is sufficient to react with a significant fraction of the trace elements to form chlorides that are more volatile than the elemental or oxide form of the metals themselves. But, the simultaneous presence of significant amount of sulfur in the fuel can reduce chlorine resulted problems. Introducing sulfur-containing materials, such as ammonium sulfate or ammonium bisulfate (U.S. Pat. No. 6,817,181), sulfur dioxide (JP6180104), high sulfur-containing fuel (JP2006064251), also appears to be effective in mitigating chlorine resulted corrosion issues (by sulfation reaction, $2AlkCl+SO_2+H_2O+\frac{1}{2}O_2=Alk_2SO_4+2HCl$, where Alk is the alkali metal).

Therefore, a second sorbent that can effectively retain the HCl (originally in gas phase and liberated from the above reaction), and in some cases a third sorbent for sulfur capture, should be added to the engineered feed stock to simultaneously retain sulfur, chlorine and alkali (or trace) metals.

Co-firing or co-gasifying two distinct fuels can sometimes turn otherwise disadvantages of the individual fuel into advantages for the combination. For instance co-firing higher sulfur/low chlorine coal balances the normally low sulfur/high chlorine/alkali metals of biomass fuels having at least the following benefits:

a. Sulfur in coal helps reduce alkali salts formation and corrosive deposits, which cause the most aggressive high temperature corrosion. Selecting the co-firing ratio so that the molar ratio of S/Cl>4 and S/(Na+K+Cl)>5 effectively prevents corrosion from chlorine and alkali chlorides.

b. Base metal elements that are in abundance in the biomass ash help retain sulfur and chlorine. In addition, Na, K, Fe, iron chloride, etc. are catalysts for coal steam gasification and allow for low temperature operation of the system. On the other hand, silica and alumina rich coal ash can help retain harmful trace metals at high temperatures, for example:

$$2PbO + SiO_2 \longrightarrow Pb_2SiO_4(s)$$

$$CdO + SiO_2 \longrightarrow CdSiO_3(s)$$

$$CdO + Al_2O_3 \longrightarrow CdAl_2O_4(s)$$

$$PbCl_2 + Al_2O_3 \cdot 2SiO_2 + H_2O \longrightarrow PbO \cdot Al_2O_3 \cdot 2SiO_2(s) + 2HCl(g)$$

c. Biomass normally contains lower fuel-nitrogen (0.1-0.5%) than coals (1.5%), thus lowers potential of NOx production. Also, because biomass contains more volatile nitrogen (coal contains more char nitrogen) which is more likely to end up being $NH_3$ than HCN, formation of $N_2O$, a GHG, is reduced.

d. Chlorine in the biomass oxidizes Hg to form $HgCl_2$ ($Hg^2$) and promotes formation of particulate Hg, which is less volatile than elemental $Hg^0$, and thus can be captured in downstream bag-house equipment and other dust collecting equipment.

e. Co-firing biomass can increase carbon combustion efficiency due to increased volatile matter in the mixed fuel than coal alone.

Co-combustion of coal and waste products could help reduce the emission of dioxin below the statutory limit especially in presence of sulfur in the fuel, because chlorine is effectively retained before it is oxidized to elemental chlorine ($Cl_2$)

Operating Conditions can Affect the Feed Stock Composition

Some pollutants are more volatile, or more reactive, with one particular sorbent in a reducing atmosphere, as opposed to under an oxidizing atmosphere. These differences often result in different process characteristics and sorbent utilization performance. For some sorbents, if sintering is expected to occur at high temperatures, the risk of sintering could be prevented or minimized in a reducing environment.

Lower operating temperature helps reduce chlorine corrosion, and ash slag formation. However, depending on the process characteristics, it could also lead to other issues such as reduced carbon conversion, reduced sorbent utilization and increased tar production, etc. It may also lead to lower fuel conversion and lower system performance. Therefore, selecting one or more sorbents that can work effectively under desired operating conditions is vital. In some embodiments, an operating temperature of about 800-850° C. seems to be optimal. This temperature range is especially true for biomass fuels. Under this temperature, alkali-rich ash does not fuse because alkali metals are not vaporized. Sodium-based sorbent works effectively, carbon conversion is high enough and tar formation is minimal. Also, sorbents for capturing sulfur or chlorine may also have catalytic ability to allow gasification or combustion to occur at a reduced temperature. This effect is especially important for fossil fuels.

Reactivity of the Sorbent and Characteristics of the by-Product Affect the Feed Stock Composition Reactivity or effectiveness of the selected sorbent(s) is certainly an important factor to be considered, and it is also important to understand that the reactivity varies depending on the reaction conditions. For example, lime and hydrated lime are more reactive in oxidizing conditions than limestone, because the latter suffers serious micro-pores plugging due to formation of low-pores calcium sulfate (i.e., molar volume is increased from 36.9 cm³/mole of limestone to 46.0 cm3/mole of $CaSO_4$) around the active limestone core. Under a reducing environment, however, the by-product, CaS, is more porous than limestone (i.e., molar volume is reduced from 36.9 cm3/mole of limestone to 27.9 cm3/mole of CaS). In addition, CaS has a melting temperature of 2,525° C. compared to 1,460° C. of $CaSO_4$. It is clear that removing sulfur by calcium-based sorbent, especially limestone, in reducing conditions is advantageous in some embodiments. But, if the reactor temperature is low, the reactivity of calcium-based sorbents is limited, so that more reactive sodium-based sorbents or other sorbents become more favorable.

Sodium-based sorbents are often more reactive than calcium-based sorbents, especially with sulfur and chlorine. But, the by-products (e.g., $Na_2S$, $Na_2SO_4$) generally have low melting temperature, though NaCl (801° C.) is slightly higher than $CaCl_2$ (772° C.). Therefore, if a second sorbent is added to simultaneously capture alkali metals, trace metals, sulfur or chlorine and increase ash melting temperature, more reactive sodium-based sorbents may be used in these embodiments.

Figure 5:
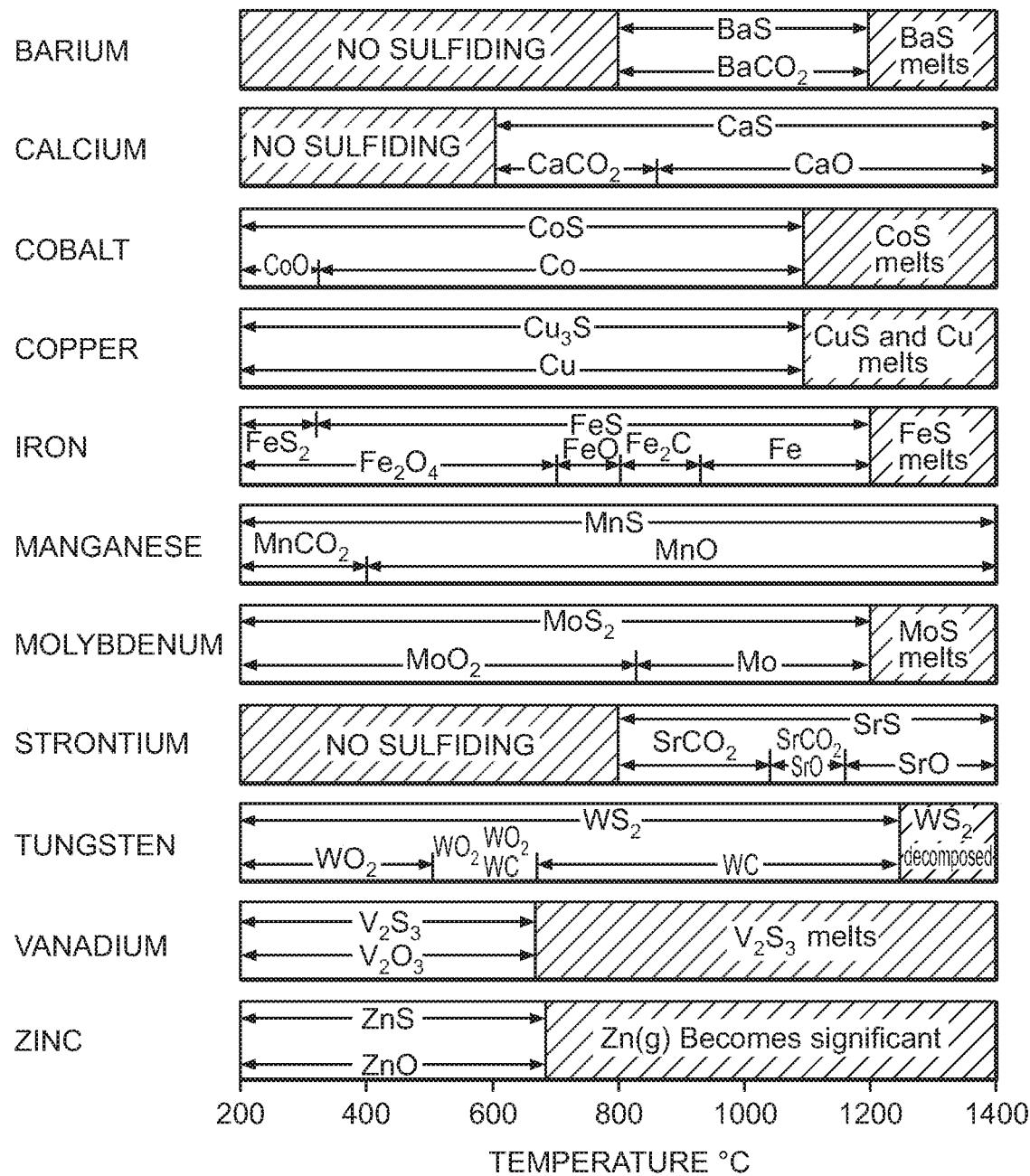
FIG. 5 is a graphic representation of the temperature ranges for various sorbents and their reactivity to hydrogen sulfide.

Iron is proven to be reactive with sulfur and chlorine. It is widely used to manufacture boiler heater tubes which, as a result, are prone to chlorine and sulfur corrosion. By leveraging the well established iron corrosion mechanism, the iron filings can be utilized as an artificial corrosion receptor to effectively control chlorine gas, HCl, and alkali chlorides, so prevent high temperature corrosion of actual boiler tubes, and dioxin formation. Moreover, the main compound in iron filings, iron oxides, have a wide range of temperature reacting with sulfur and chlorine. (see Westmoreland, P. R. et. al "Evaluation of candidate solids for high temperature desulfurization of low-BTU gases" Env. Sci. Technol. 10(7) 659-661, 1976.) Finally, as can be seen in FIG. 5 (see Westmoreland, 1976), sulfur has a wide reactivity profile with many different metals and this reactivity at different temperatures can be used to design a feed stock with a sorbent, or multiple sorbents, that will be effective at a given temperature and not form a melt that could possibly fowl the equipment.

The use of iron filings, therefore has many advantages. Iron oxides, unlike sodium based sorbents, do not have deposit issues because the iron chloride and iron sulfide compounds have higher melting points and are less prone to fouling the boiler. Iron filings from foundry plants are often disposed of, at a cost, in municipal landfills as a waste. They are, therefore, inexpensive, because they are free or can be obtained at a profit, i.e., the foundries will pay to have them removed.

The iron filings that come from foundry plants may contain iron in different forms, such as Fe, FeO, $Fe_2O_3$ or $Fe_3O_4$, each of which can be used directly or pretreated. The iron waste can be used alone, or mixed with some other sorbents, to enhance, improve one or more aspects of the performance. Such sorbents may include, but not limited to, sodium sesquicarbonate (Trona), sodium bicarbonate, sodium carbonate, zinc ferrite, zinc copper ferrite, zinc titanate, copper ferrite aluminate, copper aluminate, copper manganese oxide, nickel supported on alumina, zinc oxide, iron oxide, copper, copper (I) oxide, copper (II) oxide, limestone, lime, iron filings, Fe, FeO, $Fe_2O_3$, $Fe_3O_4$, $CaCO_3$, $Ca(OH)_2$, $CaCO_3 \cdot MgO$, silica, alumina, china clay, kaolinite, bauxite, emathlite, attapulgite, coal ash, egg shells, and Ca-montmorillonite.

Based on the inventors' analysis with the iron filings, there is about 70% of iron content, primarily in the chemical form of iron(II,III) oxide. $Fe_3O_4$, which exhibits permanent magnetism and is ferrimagnetic (and it is sometimes formulated as $FeO \cdot Fe_2O_3$). When it reacts with $H_2S$ or HCL, the following chemical reactions are assumed to take place (the reaction rate, or kinetics, are not considered here):

$$Fe_3O_4 + 4H_2S = Fe_3S_4 + 4H_2O$$

$$Fe_3O_4 + 8HCl = FeCl_2 + 2FeCl_3 + 4H_2O$$

Therefore, it theoretically requires 1.70 and 0.79 unit of weight $Fe_3O_4$ to react with 1 unit weight of $H_2S$ and HCl, respectively (in a molar ratio, Fe/S is ¾, and Fe/Cl is ⅜). Though iron filings of primarily $Fe_3O_4$ were tested below, iron and its other oxides such as FeO, $Fe_2O_3$, $Fe(OH)_2$, $Fe(OH)_3$, are also useful in removing $H_2S$ and HCl.

There also many known high temperature sulfur sorbents that are part of the present invention. For example, the following compounds are known to react with sulfur at high temperature: zinc ferrite, zinc copper ferrite, zinc titanate, copper ferrite aluminate, copper aluminate, copper managanese oxide, nickel supported on alumina, zinc oxide, iron oxide, copper, copper oxide, limestone, and lime.

Exemplary Advantages of the Invention

Below is a description of some representative advantages of invention described herein. While these particular advantages are below, it would be obvious to those skilled in the art that various other advantages arise from this invention without departing from the spirit and scope of the disclosure.
1. Emission Controls—Efficient, Cost Effective, Emission Controls Allowing for Co-Use with Other Fuels, and Fuel Flexibility.

Integration of sorbents with the engineered fuel feedstock is a powerful way to control hazardous air pollutants (HAPs) emissions from thermal conversion processes. With sorbents uniformly distributed within the fuel, intimate contact and sufficient retention time can be readily achieved, and therefore leading to high sorbent utilization efficiency and HAPs control efficiency.

Sorbent containing engineered feedstock can be designed to meet the air emission targets without post-conversion gas treatment devices when the engineered fuel is solely used. For existing facilities where a fossil or biomass fuel (such as coal, wood, hog fuel, animal wastes, etc) is being used, the engineered fuel can be designed to substitute a portion of the existing fuel, and have ability to control air emissions from both the engineered fuel and the substituted fuel. Obviously, co-use of the engineered fuel with other fuels that may struggle to meet the increasingly stringent environment regulation requirements is a cost effective and yet efficient retrofit approach to allow them meet the goal but without extensive capital investments to install the post-combustion emission control processes.

With sorbent in the engineered fuel feedstock, it will allow beneficial use of materials that would otherwise likely have to be avoided because of their inherent nature of causing environmental or operational problems, such as PVC, hog fuel, animal wastes and low rank coals. It is unpractical to assume that these environmental and/or operational harmful, but still valuable as fuel, materials could be thoroughly removed from the waste stream even if a costly and dedicated sorting and separation process would be in place, i.e. containments of such materials in the fuel feedstock can be a reality. Using sorbents in the engineered fuel therefore not only ensure these containments not to cause environmental and/or operational problems, but also could allow beneficially use of these materials and therefore avoid expensive pre-sorting and separation.

In addition to sulfur and chlorine, suitable sorbents can be integrated with the engineered fuel feedstock to control heavy metals emissions, which are very expensive with post combustion control approaches.
2. Corrosion Prevention/Minimization Because of the nature of biomass based fuel, i.e., high chlorine and alkali metal contents, equipment corrosion (i.e., super-heater tubes, economizer, air heater, etc.) has been the major challenge in operating biomass based fuel boilers and power plants. High temperature chlorine corrosion in biomass and waste firing boilers has been causing frequent and extended plant downtime for steam tubes repair and replacement, which not only requires expensive labor and materials, but also results in extra costs resulted from loses in power revenue and costs in waste-by pass to landfill.

Combining sorbents with the engineered fuel would capture and retain the corrosive components in the ash, and therefore prevent them from entering into the gas stream and avoid them interacting with the downstream equipment. As the equipment corrosion is prevented or minimized, the plant availability will be increased, which brings significant economic benefits such as reduced operation and maintenance costs and increased power revenue.
3. Improved Process Operation Because of high alkali metal content the biomass and waste fuels are prone in formation of slagging, agglomerations, or deposits when they are used as fuel in gasifiers or combustors. These problems not only increase the operational difficulty, lead to system downtime, but also reduces heat transfer rate due to formation of deposits and scales on the heat transfer surfaces.

These operational issues can be greatly minimized with the engineered fuel feedstock having additives to change, adjust or improve the fuel ash characteristics such as fusion temperature. Adding suitable additives, such as MgO and/or aluminum silicates like materials, even coal ashes, would be able to convert the biomass ash to coal-like ash, which has high fusion temperature and not expect to cause slagging in operation temperatures.
4. Improved Process Performance Compared to the typical coal fired power plants which typically have electrical efficiencies of 30-40%, the biomass and waste derived fuel fired power plants only produce electricity with efficiencies of about 20%. One of the biggest limiting factors that contribute to this difference is that biomass and waste derived fuels have high chlorine and alkali metal contents, which limit the boilers to operate at relatively low steam temperature and pressure (750° F., and 650-800 psig, typically) to control and minimize the high temperature corrosion (which increases exponentially when flue gas temperatures are higher than approx. 2,000° F.). These compares to approx. 1000° F. and 3,500 psig for coal fired power plants.
5. Extending the Coal Power Plant Lifetime With air emission standards continuing to become more and more stringent, for example EPA's new transport rule, the vast majority of coal-fired power plants in the U.S. will need to make a critical decision, i.e., either spending multimillion dollars to retrofit their emission control system to meet the compliance, or simply shutdown the power plant to avoid that expense. (see Proposed Transport Rule 75 FR 45210). For a typical 500 MW coal fired plant, the retrofit cost to install flue gas desulfurization system in order to comply with the regulation would cost an estimated $75 million dollars with an additional approximately $6.8 million dollars in annual operation and maintenance (based on Energy Information Administration's (EIA) average Flue Gas Desulfurization (FGD) cost data). Clearly, the use of engineered fuel feed stocks of the present invention will not only avoid the above retrofit cost, but would also allow the plant to extend its operational life.

With the engineered fuel feedstock containing corrosion preventive sorbents and additives, the high temperature corrosion can be prevented or minimized, as a result would allow the biomass and waste derived fuel fired power plants to operate at elevated steam temperature and pressure and thus increase the power generation efficiency.

EXAMPLES

Reference will now be made to specific examples some of which illustrate the invention. It is to be understood that the examples are provided to illustrate preferred embodiments and that no limitation to the scope of the invention is intended thereby.

General Procedures

The feed stock used in these tests below was made from MSW components, including paper, cardboard, magazines, and plastics, using procedures described in U.S. patent application Ser. No. 12/492,096. A full characterization of the prepared feed stock is provided below:

TABLE 1

Analysis of the baseline feed stock (wt. %, as received basis)

| | |
|---|---|
| Moisture | 4.63 |
| Volatile matter | 73.14 |
| Fixed carbon | 16.56 |
| Ash | 5.67 |
| Carbon | 57.76 |
| Hydrogen | 7.34 |
| Nitrogen | 0.14 |
| Oxygen | 18.93 |
| Sulfur | 3.5 |
| Chlorine | 2.03 |

This feed stock is referred to as baseline feed stock, and it has no pollutant control sorbents added. In the experiments below, varying amount of sorbent are added in order to control pollutant emissions.

Since under gasification (or reducing) conditions at temperatures of 800-850° C., the majority of sulfur and chlorine would be converted to $H_2S$ (with minor amount of COS) and HCl (typically about 10-50% Cl in fuel is converted to HCl, see S. V. B. van Paasen, M. K. Cieplik and N. P. Phokawat, "Gasification of Non-woody Biomass Economic and Technical Perspectives of Chlorine and Sulphur Removal from Product Gas (Non-confidential version)," ECN-C-06-032), the amount of sorbent is determined based on the chemical reactions of $H_2S$ and HCl with the specific sorbent being investigated. For instance, when Trona is used as sorbent, the following chemical reactions occur:

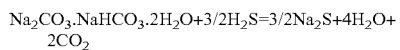

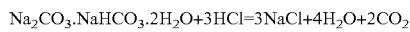

According to the chemical stoichiometry, removal of one unit weight of $H_2S$ and HCl would require 4.42 and 2.07 times as much Trona by weight (or 1 mole of sulfur needs 2.0 moles of sodium contained in Trona, and 1 mole of Cl needs 1 mole of sodium contained in Trona). Similarly, when lime is used, the following chemical reactions occur:

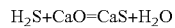

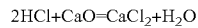

Again according to this reaction, removal of one unit weight of $H_2S$ and HCl would require 1.65 and 0.77 times as much calcium oxide by weight (or 1 mole of sulfur needs 1 mole of calcium contained in lime, and 1 mole of Cl needs 0.5 mole of calcium contained in lime)

After components for the engineered feed stock are selected as discussed above, they are shredded in a low speed shredder and then mixed mechanically. Sorbent is then added to the mixture according to the present invention. Afterwards the mixture is densified using a pelletizer. If the moisture content needs to be increased, water is added during the mixing step or during the pelletization process. A small sample of the feed stock is taken and dried in an temperature controlled and vented oven to confirm the moisture content. The mixed engineered feed stock is then subjected to gasification as described above.

Gasification tests were performed at a laboratory scale stratified downdraft gasifier. The gasifier has an inside diameter of 4 inches and a height of 24 inches above a perforated grate. There are four Type-K thermocouples installed along the gasifier, 1", 7", 19" above the grate and 4" below the grate. The real-time temperatures were recorded by a data logger and software (Pico Technology Inc., Cambridgeshire, UK). A syngas sampling train, consisting of two water scrubbers, and a vacuum pump was used for taking syngas samples, and were analyzed by an online Rosemount Gas Analyzer (Model MLT2, Emerson Process Management, Germany), to obtain volumetric fractions of $H_2$, $N_2$, CO, $CO_2$ and $CH_4$ and $O_2$. To measure the $H_2S$ and HCl concentrations, the Drager tubes of different scales (Draeger Medical Inc. Telford, Pa.) were selected. To ensure reproducibility, $H_2S$ and HCl were measured a multiple times each time and repeated for three to four times during the steady operation. A dry gas test meter was installed in the air entrance to measure the air intake rate. A schematic representation of the experimental set up is shown in FIG. 1.

Effect of Various Amounts of Sorbent on the Production of Sulfur and Chlorine Pollutants Upon Gasification of Fuel Feed Stocks Example 2

Figure 2:
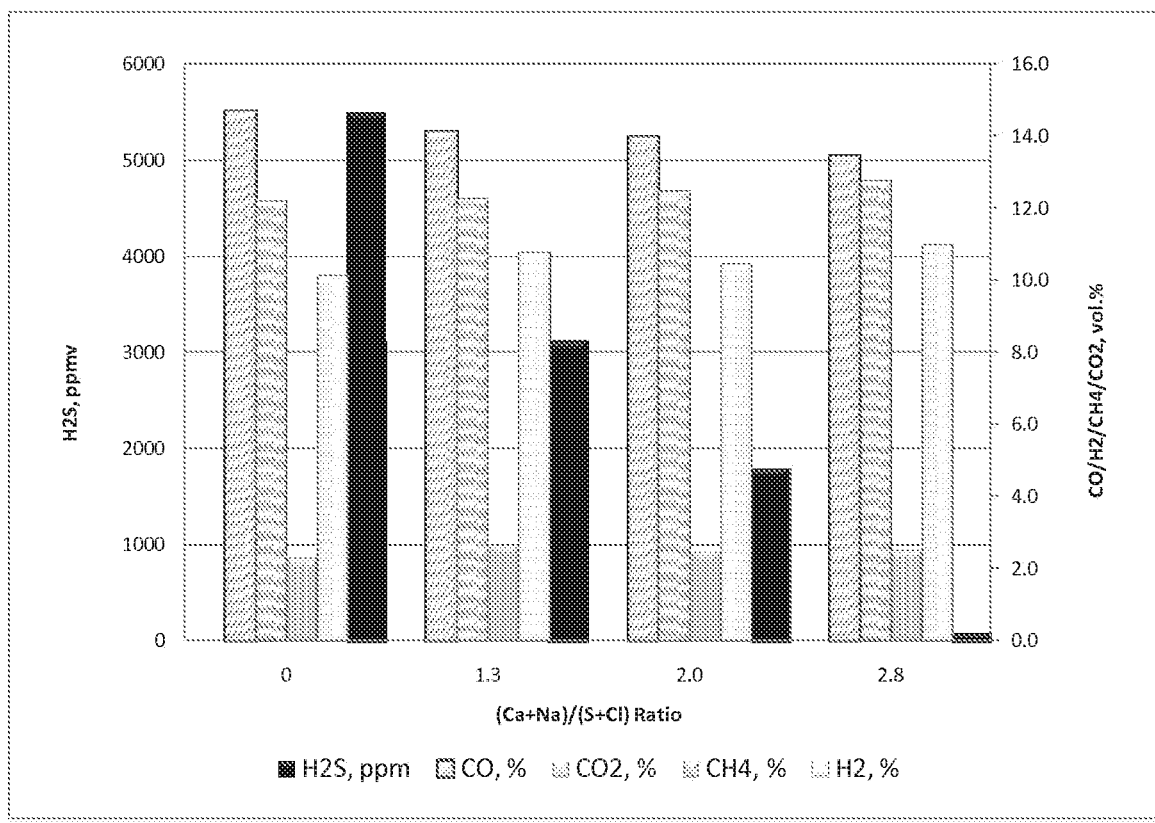
FIG. 2 discloses the syngas composition from feed stocks without and with sorbent.

The first series of tests were conducted with the baseline feed stock, and feed stocks with different amounts of Trona and lime sorbents added. The results are summarized in Table 2 and FIG. 2. The ratio of sorbent to feed stock was calculated as follows:

For a unit weight of the feeds tock, the amounts of sulfur and chlorine are calculated based on their composition (i.e. weight percentage as listed in Table 1). The weights of sulfur and chlorine are then divided by the molecular weights of sulfur (i.e. 32.07 gram/mole) and chlorine (i.e. 35.45 gram/mole) to obtain the moles of sulfur and chlorine. Similarly, the added weight of sorbent are divided by the molecular weight (i.e. 226.03 gram/mole for Trona, 56.08 for CaO, 74.09 for hydrated lime) to obtain the moles of the sorbent. In case of Trona, one mole of Trona contains 3 moles of sodium, and in case of hydrated lime, one mole of hydrated lime contains 1 mole of calcium. Thus, the total Ca and Na can be calculated. Dividing the total moles of Ca and Na by the total moles of S and Cl yields the ratio of (Ca+Na)/(S+Cl), which were listed in Table 2.

In some cases, the stoichiometric ratio is used. In this case, the stoichiometric requirement of sorbent (in moles of Ca, or Na, etc.) is calculated based on the specific chemical reaction involved, such as those provided above. Then, based on the preferred stoichiometric ratio, the total required moles of sorbent is calculated by multiplying the stoichiometric requirement of sorbent by the preferred stoichiometric ratio. The result can be then converted to the weight of sorbent by using the sorbent molecular weight. Knowing the total weight of the feed stock and the total sorbent weight, the weight percentage (or wt. %) of the sorbent in a sorbent containing feed stock can be readily calculated.

TABLE 2

Experimental results from Example 1

| (Ca + Na)/(S + Cl) | 0 | 1.3 | 2.0 | 2.8 |
|---|---|---|---|---|
| wt % CO | 14.7 | 14.2 | 14.0 | 13.5 |
| wt % CO2 | 10.1 | 10.8 | 10.5 | 11.0 |
| wt % CH4 | 2.3 | 2.7 | 2.5 | 2.5 |
| wt % H2 | 12.2 | 12.3 | 12.5 | 12.8 |
| Total | 60.6 | 60.1 | 60.5 | 62.9 |
| H2S, ppm | 5,500 | 3,129 | 1,800 | 90 |
| Normalized H2S | 100% | 56.9% | 32.7% | 1.6% |

Example 1 demonstrates that with the same baseline feed stock, the syngas composition of $H_2$, CO, $CO_2$ and $CH_4$ are fairly identical, but with additional amounts of sorbent pre-blended into the feed stock, the $H_2S$ concentration in syngas is inversely proportional to the amount of sorbent in the feed stock. At a molar ratio (Ca+Na)/(S+Cl) of approximately 3, over 95-98% of $H_2S$ can be removed from syngas compared to the untreated feed stock.

Example 2

Figure 3:
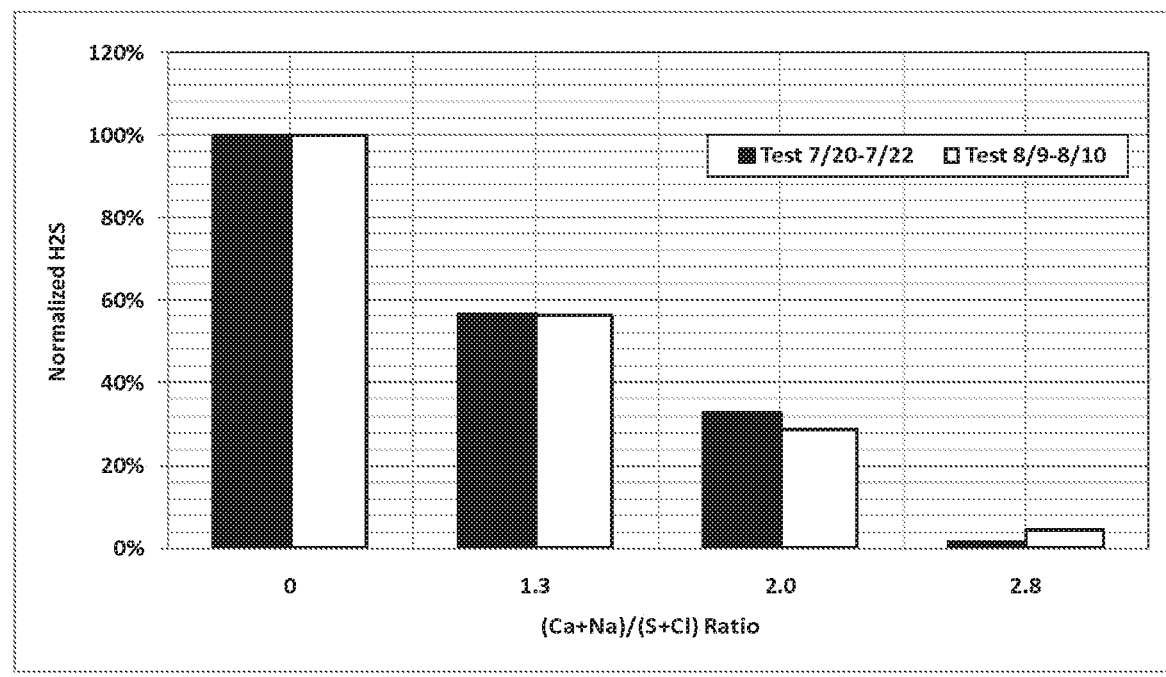
FIG. 3 is a graphic comparison of the results of examples 2 and 3 and demonstrates the inverse relationship between sorbent content in the feed stock and hydrogen sulfide in the syngas.

A second series of experiments was carried out with the same feed stocks as in Example 1. The results from Example 1 are compared with those of Example 2, and summarized in FIG. 3. FIG. 3 demonstrates that in both examples increasing the molar amount of sorbent in the feed stock reduces the amount of $H_2S$ in the syngas. Based on the experimental results, sorbent integrated with the engineered feed stock can drastically reduce sulfur emissions from the gasification process.

Example 3

In addition to analyzing the syngas for hydrogen sulfide in the previous examples, the gas was also measured for HCL. It was found that there was no detectable HCl present in the syngas produced. Furthermore, the condensate collected from the gas-liquid separator, which is produced by the syngas sample cooler, was measured with a pH meter and total Chlorine meter. The measured pH was between 1 and 3, suggesting the condensate was acidic and the total chlorine was measured between 0-4 ppm, suggesting very little chlorine in the condensate, both of which are indicative of very little HCl present in syngas.

Example 4

While it is important to measure the content of sulfur and chlorine in the syngas produced during gasification, that is not the only means of measuring the effectiveness of the sorbent treatment of the present invention. In Example 4, samples of the ash from feed stocks with varying amounts of integrated sorbent were analyzed for sulfur and chlorine content.

TABLE 3

Sulfur and chlorine contents in ash samples

| Sorbent (Ca + Na)/(S + Cl) | 0 | 1.3 | 2.0 |
|---|---|---|---|
| ppm Sulfur (by ASTM D4239) | 1.96 | 3.30 | 4.11 |
| ppm Chlorine (by ASTM 4208) | 0.69 | 1.13 | 7.54 |

As can be seen in Table 3, when the amount of the sorbent increases, the amount of sulfur and chlorine in the ash also increases. This result demonstrates that the sorbent is capturing a greater amount of sulfur and chlorine in the ash than in the non-treated feed stock.

These results also show that calcium-based sorbent is more effective in retaining sulfur (sulfur content in ash increased from 1.96% without sorbent to 3.30% with hydrated lime, and then increased to 4.11% with Trona added). Sodium-based sorbent is more effective in retaining chlorine (chlorine content in ash increased from 1.13% without Trona to 7.54% with Trona).

In conventional furnace sorbent injection (under combustion conditions), at a molar ratio of about 3, only about 60% $SO_2$ reduction efficiency can be achieved. ("Design and Test Furnace Sorbent Injection for $SO_2$ Removal in a Tangentially Fired Boiler" Wei Zhou, Pete Maly, Joy Brooks, Santosh Nareddy, Larry Swanson, David Moyeda. Environmental Engineering Science. April 2010, 27(4): 337-345; Optimization of Trona/Limestone Injection for $SO_2$ Control in Coal-Fired Boilers, Western Research Institute, 2005.) To achieve an equivalent desulfurization performance as witnessed in the above examples, a ratio of 5-6 is typically needed.

Additional experiments are performed according to the above described examples using the following sorbent combinations at the appropriate molar ratios: Trona and MgO; Trona and kaolinie; or Trona and Silicates. Each of these combination has a similar proportional reduction of sulfur and chlorine content in the syngas produced.

Co-Gasification

It is also contemplated that the engineered feed stocks with integrated sorbent of the present invention can be co-gasified with traditional fuels such as coal and the integrated sorbent can effectively remove sulfur emissions from both the engineered fuel and the coal. For example, a first feed stock (A) was created as a baseline fuel equivalent to coal. As can be seen in Table 1 above, it has a high sulfur content. The second feed stock (B) is one that was prepared to represent a typical feed stock from MSW streams, and would be expected to have the following characteristics shown in Table 4:

TABLE 4

Calculated Profile of Feed Stock B as a Wt %

| Moisture | 16.7 |
|---|---|
| Volatile matter | 71.2 |
| Fixed carbon | 9.8 |
| Ash | 2.4 |
| Carbon | 43.7 |
| Hydrogen | 6.1 |
| Nitrogen | 0.50 |
| Oxygen | 30.0 |
| Sulfur | 0.19 |

TABLE 4-continued

Calculated Profile of Feed Stock B as a Wt %

| Chlorine | 0.44 |
|---|---|
| HHV (Btu/lb) | 8,392 |

Also, feed stocks C and D were prepared from feed stock B, but with 9% Trona and 27% Trona added respectively.

TABLE 5

The results of co-gasifying tests

|  | A | B | A + B | A + C | A + D |
|---|---|---|---|---|---|
| wt % CO | 13.4 | 16.5 | 14.6 | 11.4 | 12.0 |
| wt % CO2 | 11.5 | 10.1 | 10.0 | 14.4 | 11.6 |
| wt % CH4 | 3.0 | 2.0 | 2.0 | 3.0 | 2.3 |
| wt % H2 | 9.7 | 16.6 | 15.2 | 15.1 | 9.0 |
| wt % O2 | −0.1 | 0.2 | 0.3 | 0.0 | −0.1 |
| Total | 62.5 | 54.6 | 57.9 | 56.2 | 65.3 |
| H2S, ppm | 3,300 | 85 | 1,350 | 1,260 | 550 |
| Normalized H2S | 100% | 2.6% | 40.9% | 38.2 | 16.7% |
| Percent of residual sulfur |  |  | 100% | 99.3% | 40.7% |

As can be seen in Table 5, five different experiments were performed. First, the high sulfur feed stock (A) was gasified to give a baseline for that material and then the same was done for feed stock B. Then, a co-gasification test was conducted in which 50% A and 50% B were well mixed and loaded into the gasifier and the syngas analyzed. The measured $H_2S$ in the syngas averaged to about 1,350 ppmv, which is a 59% reduction of the sulfur content compared to gasification with only feed stock A. This result demonstrates that co-gasifying or co-firing a low sulfur fuel with a high sulfur fuel can effectively reduce sulfur emissions on its own.

Figure 4:
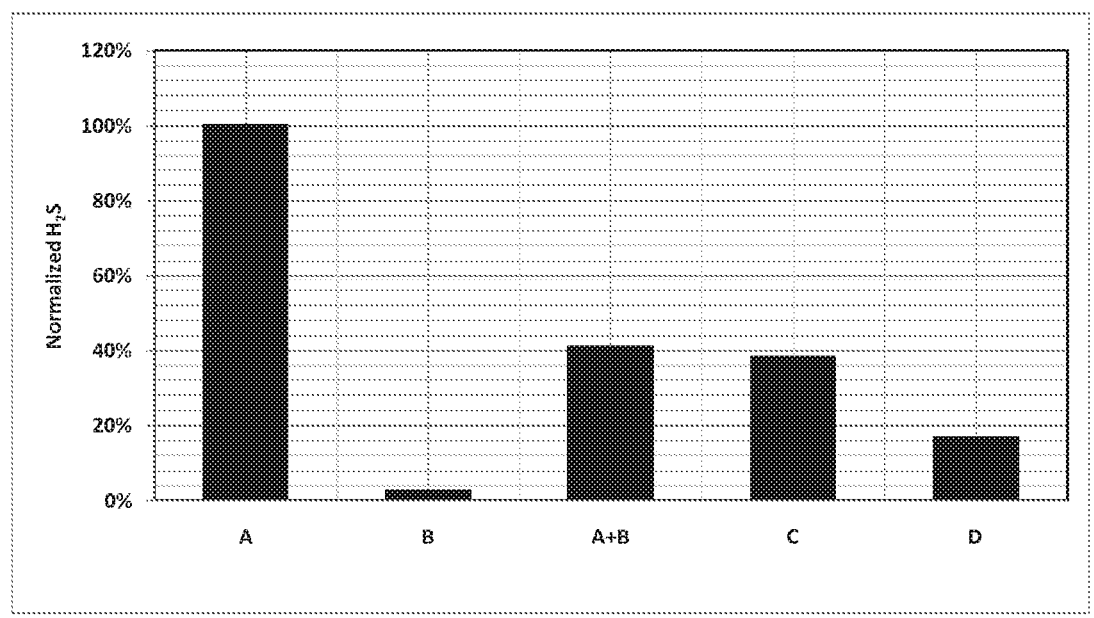
FIG. 4 is a graphic representation of the normalized hydrogen sulfide. concentrations measured during the co-gasification of coal and sorbent-treated feed stock.

Next, 50% of feed stock A was mixed with 50% feed stock C in one experiment and 50% feed stock A was mixed with 50% feed stock D in another experiment. The experimentally measured $H_2S$ in the syngas was 1,260 ppmv and 550 ppmv, respectively, which represents about 62% and 83% reduction in $H_2S$ production compared to baseline feed stock A, or 7% and 59% reduction compared to co-gasifying without sorbent (i.e., 50% feed stock A+50% feed stock B). FIG. 4 graphically displays the relative reduction in the amount of sulfur in each experiment.

Based on these results one can conclude that co-gasifying or co-firing a sorbent pre-integrated engineered feed stock with other fuels, such as coal, oil, or natural gas, can effectively remove sulfur emissions from both the engineered fuel and coal. The appropriate amount and character of the sorbent added to the engineered feed stock can be determined based on the underlying chemical reactions with respect to the specific sorbent and characteristics of both fuels (i.e., sulfur and chlorine contents).

Additional Examples

An additional series of tests were performed analyzing the effectiveness of iron filings at removing sulfur and chlorine from an engineered feed stock. The same material as described in Table 1 was used in the examples below. To this baseline feed stock, iron filings were added according to the following parameters: 1.70 and 0.79 unit of weight $Fe_3O_4$ to react with 1 unit weight of $H_2S$ and HCl, respectively (in a molar ratio, Fe/S is ¾ and Fe/Cl is ⅜). Based on these reaction mechanism, and the purity of iron filings, the total amount iron filings added to the engineered fuel feed stock in this experiment was determined. The results are described below in Table 6:

| Experiment # | 0% Iron Filings i | 7% Iron Filings ii | 14% Iron Filings iii | 19% Iron Filings iv |
|---|---|---|---|---|
| H2S, ppmv | 5,500 | 2,100 | 365 | 220 |
| HCl, ppmv | 2,000 | 700 | 250 | 100 |
| H2S, Normalized | 100.0 | 38.2 | 6.6 | 4.0 |
| HCl, Normalized | 100 | 35.0 | 12.5 | 5.0 |
| Stoich | 0 | 1.0 | 2.0 | 3.0 |
| Iron Filings, wt. % | 0.0% | 7.0% | 13.5% | 18.5% |
| Fe/(S + Cl) | 0 | 0.53 | 1.10 | 1.59 |

As can be seen in Table 6, with an increasing amount of iron filings there is a proportional reduction in the level of hydrogen sulfide and hydrogen chloride in the syngas stream. Therefore, it is evident that iron filings are acting as an effective sorbent for both sulfur and chlorine.

While particular embodiments described herein have been illustrated and described, it would be obvious to those skilled in the art that various other changes and modifications can be made without departing from the spirit and scope of the disclosure. It is therefore intended to cover in the appended claims all such changes and modifications that are within the scope of this invention.

We claim:

1. A method of producing an engineered fuel feed stock comprising at least one fiber component and at least one plastic component, the method comprising:
   a) selecting a plurality of components from a waste stream, the plurality of components including the at least one fiber component and the at least one plastic component, which plurality of components in combination have chemical molecular characteristics comprising:
      a carbon content of between 30 wt. % and 80 wt. %,
      a hydrogen content of between 3 wt. % and 10 wt. %,
      a volatile matter content of 40 wt. % to 80 wt. %, and
      an ash content of less than 10 wt. %;
   b) combining the selected components of a) and a sorbent to form the engineered fuel feed stock, wherein the engineered fuel feed stock contains biodegradable waste and non-biodegradable wastes.

2. The method of claim 1, further comprising:
   c) adding additional fuel components to meet the desired chemical molecular characteristics of a).

3. The method of claim 2, wherein the additional fuel components include biomass.

4. The method of claim 3, wherein the biomass is wood.

5. The method of claim 1, further comprising:
   d) comminuting the engineered fuel feed stock.

6. The method of claim 1, further comprising:
   e) densifying the engineered fuel feed stock.

7. The method of claim 1, wherein the sorbent is selected from the group consisting of sodium sesquicarbonate (Trona), sodium bicarbonate, sodium carbonate, zinc ferrite, zinc copper ferrite, zinc titanate, copper ferrite aluminate, copper aluminate, copper manganese oxide, nickel supported on alumina, zinc oxide, iron oxide, copper, copper (I) oxide, copper (II) oxide, limestone, lime, Fe, FeO, $Fe_2O_3$, $Fe_3O_4$, iron filings, $CaCO_3$, $Ca(OH)_2$, $CaCO_3.MgO$, silica, alumina, china clay, kaolinite, bauxite, emathlite, attapulgite, coal ash, egg shells, wood ash, coal ash, and Ca-montmorillonite.

8. The method of claim 7, wherein the sorbent is obtained from a renewable source.

9. The method of claim 7, wherein the sorbent is in an amount of between 0.1% (weight sorbent/weight fuel feed stock (w/w)) and 50% (w/w).

10. The method of claim 9, wherein the sorbent is in the amount of between 1% (w/w) and 20% (w/w).

11. The method of claim 1, wherein the ash content is less than 8 wt. %.

12. The method of claim 11, wherein the ash content is less than 6 wt. %.

13. The method of claim 12, wherein the ash content is less than 5 wt. %.

14. The method of claim 1, wherein the engineered fuel feed stock contains substantially no glass, metals, grit, and noncombustible waste.

15. The method of claim 1, wherein the volatile matter content is between 50 wt. % and 70 wt. %.

16. The method of claim 15, wherein the volatile matter content is about 60 wt. %.

17. The method of claim 1, wherein the engineered fuel feed stock has a HHV of between 3,000 BTU/lb and 18,000 BTU/lb.

18. The method of claim 17, wherein the HHV is between 5,000 BTU/lb and 13,000 BTU/lb.

19. The method of claim 18, wherein the HHV is between 8,000 BTU/lb and 10,000 BTU/lb.

20. The method of claim 1, wherein the engineered fuel feed stock has a moisture content of between 10 wt. % and 30 wt. %.

21. The method of claim 20, wherein the moisture content is between 10 wt. % and 20 wt. %.

22. The method of claim 1, wherein the engineered fuel feed stock has a moisture content of between 1 wt. % and 10 wt. %.

23. The method of claim 1, wherein the engineered fuel feed stock has a sulfur content of less than 0.5 wt. %.

24. The method of claim 1, wherein the engineered fuel feed stock has a chlorine content of less than 1 wt. %.

25. The method of claim 1, wherein the engineered fuel feed stock has an H/C ratio of between 0.025 and 0.20.

26. The method of claim 1, wherein the engineered fuel feed stock has an O/C ratio of between 0.01 and 1.0.

27. The method of claim 1, wherein the carbon content is between 40 wt. % and 60 wt. %.

28. The method of claim 1, wherein the waste stream is a processed MSW waste stream.

29. The method of claim 1, wherein the waste stream is a processed industrial waste stream.

30. The method of claim 1, wherein the engineered fuel feed stock consists essentially of fiber, plastic, and sorbent.

31. A method of producing an engineered fuel feed stock comprising at least one fiber component and at least one plastic component, the method comprising:
  a) separating a plurality of MSW streams into a plurality of MSW waste components based on chemical molecular characteristics;
  b) selecting the plurality of the MSW waste components, the plurality of components including the at least one fiber component and the at least one plastic component, which plurality of MSW components in combination have chemical molecular characteristics comprising:
    a carbon content of between 30 wt. % and 80 wt. %,
    a hydrogen content of between 3 wt. % and 10 wt. %,
    an ash content of less than 10 wt. %, and
    a moisture content of between 10 wt. % and 30 wt. %;
  c) combining the selected components of step a) and a sorbent to form the engineered fuel feed stock, wherein the engineered fuel feed stock contains biodegradable waste and non-biodegradable wastes.

32. The method of claim 31, further comprising:
  d) adding additional fuel components to meet the desired chemical molecular characteristics of b).

33. The method of claim 32, wherein the additional fuel components include biomass.

34. The method of claim 33, wherein the biomass is wood.

35. The method of claim 31, further comprising:
  e) comminuting the engineered fuel feed stock.

36. The method of claim 31, further comprising:
  f) densifying the engineered fuel feed stock.

37. The method of claim 31, wherein the sorbent is selected from the group consisting of sodium sesquicarbonate (Trona), sodium bicarbonate, sodium carbonate, zinc ferrite, zinc copper ferrite, zinc titanate, copper ferrite aluminate, copper aluminate, copper manganese oxide, nickel supported on alumina, zinc oxide, iron oxide, copper, copper (I) oxide, copper (II) oxide, limestone, lime, Fe, FeO, $Fe_2O_3$, $Fe_3O_4$, iron filings, $CaCO_3$, $Ca(OH)_2$, $CaCO_3.MgO$, silica, alumina, china clay, kaolinite, bauxite, emathlite, attapulgite, coal ash, egg shells, wood ash, coal ash, and Ca-montmorillonite.

38. The method of claim 37, wherein the sorbent is obtained from a renewable source.

39. The method of claim 37, wherein the sorbent is in an amount of between 0.1% (weight sorbent/weight fuel feed stock (w/w)) and 50% (w/w).

40. The method of claim 39, wherein the sorbent is in the amount of between 1% (w/w) and 20% (w/w).

41. The method of claim 31, wherein the ash content is less than 8 wt. %.

42. The method of claim 31, wherein the ash content is less than 6 wt. %.

43. The method of claim 42, wherein the ash content is less than 5 wt. %.

44. The method of claim 31, wherein the engineered fuel feed stock contains substantially no glass, metals, grit, and noncombustible waste.

45. The method of claim 31, wherein the engineered fuel feed stock has a volatile matter content of 40 wt. % to 80 wt. %.

46. The method of claim 45, wherein the volatile matter content is between 50 wt. % and 70 wt. %.

47. The method of claim 31, wherein the engineered fuel feed stock has a HHV of between 3,000 BTU/lb and 18,000 BTU/lb.

48. The method of claim 47, wherein the HHV is between 5,000 BTU/lb and 13,000 BTU/lb.

49. The method of claim 48, wherein the HHV is between 8,000 BTU/lb and 10,000 BTU/lb.

50. The method of claim 31, wherein the moisture content is between 10 wt. % and 20 wt. %.

51. The method of claim 31, wherein the moisture content is between 12 wt. % and 28 wt. %.

52. The method of claim 51, wherein the moisture content is between 14 wt. % and 24 wt. %.

53. The method of claim 31, wherein the engineered fuel feed stock has a sulfur content of less than 0.5 wt. %.

54. The method of claim 31, wherein the engineered fuel feed stock has a chlorine content of less than 1 wt. %.

55. The method of claim 31, wherein the engineered fuel feed stock has an H/C ratio of between 0.025 and 0.20.

56. The method of claim 31, wherein the engineered fuel feed stock has an O/C ratio of between 0.01 and 1.0.

57. The method of claim 31, wherein the carbon content is between 40 wt. % and 60 wt. %.

58. The method of claim 31, wherein the engineered fuel feed stock consists essentially of fiber, plastic, and sorbent.

59. A method of producing an engineered fuel feed stock comprising at least one fiber component and at least one plastic component, the method comprising:
   a) separating a plurality of MSW streams into MSW components;
   b) selecting a plurality of MSW components, the plurality of MSW components including the at least one fiber component and the at least one plastic component, which plurality of MSW components in combination have chemical molecular characteristics comprising:
      a carbon content of between 30 wt. % and 80 wt. %,
      a hydrogen content of between 3 wt. % and 10 wt. %,
      a volatile matter content of 40 wt. % to 80 wt. %,
      an ash content of less than 10 wt. %, and
      a moisture content of between 10 wt. % and 30 wt. %;
   c) selecting an amount of sorbent;
   d) combining the selected components of step b) and the amount of sorbent to form the engineered fuel feed stock, wherein the engineered fuel feed stock contains biodegradable waste and non-biodegradable wastes; and
   e) densifying the engineered fuel feed stock.

60. The method of claim 59, further comprising:
   f) comparing the resulting chemical molecular characteristics of the engineered fuel feed stock of d) with the chemical molecular characteristics of step b).

61. The method of claim 60, further comprising:
   g) adding additional fuel components to the engineered fuel feed stock in d).

62. The method of claim 61, wherein the additional fuel components include biomass.

63. The method of claim 62, wherein the biomass is wood.

64. The method of claim 59, further comprising:
   h) comminuting the engineered fuel feed stock.

65. The method of claim 59, wherein the sorbent is selected from the group consisting of sodium sesquicarbonate (Trona), sodium bicarbonate, sodium carbonate, zinc ferrite, zinc copper ferrite, zinc titanate, copper ferrite aluminate, copper aluminate, copper manganese oxide, nickel supported on alumina, zinc oxide, iron oxide, copper, copper (I) oxide, copper (II) oxide, limestone, lime, Fe, FeO, $Fe_2O_3$, $Fe_3O_4$, iron filings, $CaCO_3$, $Ca(OH)_2$, $CaCO_3.MgO$, silica, alumina, china clay, kaolinite, bauxite, emathlite, attapulgite, coal ash, egg shells, wood ash, coal ash, and Ca-montmorillonite.

66. The method of claim 59, wherein the sorbent is in the amount of between 0.1% (weight sorbent/weight fuel feed stock (w/w)) and 50% (w/w).

67. The method of claim 66, wherein the sorbent is in the amount of between 1% (w/w) and 20% (w/w).

68. The method of claim 59, wherein the ash content is less than 8 wt. %.

69. The method of claim 68, wherein the ash content is less than 6 wt. %.

70. The method of claim 69, wherein the ash content is less than 5 wt. %.

71. The method of claim 59, wherein the engineered fuel feed stock contains substantially no glass, metals, grit, and noncombustible waste.

72. The method of claim 59, wherein the volatile matter content is between 50 wt. % and 70 wt. %.

73. The method of claim 59, wherein the engineered fuel feed stock has a HHV of between 3,000 BTU/lb and 18,000 BTU/lb.

74. The method of claim 73, wherein the HHV is between 5,000 BTU/lb and 13,000 BTU/lb.

75. The method of claim 74, wherein the HHV is between 8,000 BTU/lb and 10,000 BTU/lb.

76. The method of claim 59, wherein the moisture content is between 10 wt. % and 20 wt. %.

77. The method of claim 59, wherein the engineered fuel feed stock has a sulfur content of less than 0.5 wt. %.

78. The method of claim 59, wherein the engineered fuel feed stock has a chlorine content of less than 1 wt. %.

79. The method of claim 59, wherein the engineered fuel feed stock has an H/C ratio of between 0.025 and 0.20.

80. The method of claim 59, wherein the engineered fuel feed stock has an O/C ratio of between 0.01 and 1.0.

81. The method of claim 59, wherein the carbon content is between 40 wt. % and 60 wt. %.

* * * * *